(12) United States Patent
Suzuki et al.

(10) Patent No.: US 8,501,965 B2
(45) Date of Patent: Aug. 6, 2013

(54) METHOD FOR PRODUCING 3-SUBSTITUTED-4-FLUOROPYRROLIDINE DERIVATIVE

(75) Inventors: Masashi Suzuki, Tochigi (JP); Muneki Nagao, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/700,772

(22) PCT Filed: May 30, 2011

(86) PCT No.: PCT/JP2011/062385
§ 371 (c)(1),
(2), (4) Date: Nov. 29, 2012

(87) PCT Pub. No.: WO2011/152354
PCT Pub. Date: Dec. 8, 2011

(65) Prior Publication Data
US 2013/0085282 A1    Apr. 4, 2013

(30) Foreign Application Priority Data

May 31, 2010   (JP) ................................. 2010-123889

(51) Int. Cl.
*C07D 207/04*   (2006.01)
(52) U.S. Cl.
USPC ........................................................ 548/566
(58) Field of Classification Search
None
See application file for complete search history.

(56) References Cited

U.S. PATENT DOCUMENTS

| 7,667,049 B2 * | 2/2010 | Gotoh et al. .................. 548/566 |
| 2005/0182052 A1 | 8/2005 | Asahina et al. |
| 2006/0281779 A1 | 12/2006 | Asahina et al. |
| 2009/0023935 A1 | 1/2009 | Gotoh et al. |
| 2009/0176824 A1 | 7/2009 | Asahina et al. |

FOREIGN PATENT DOCUMENTS

| JP | 2005-239617 | 9/2005 |
| WO | 2003/078439 | 9/2003 |
| WO | 2005/026147 | 3/2005 |
| WO | 2005/075426 | 8/2005 |
| WO | 2006/013048 | 2/2006 |
| WO | 2007/102567 | 9/2007 |

OTHER PUBLICATIONS

International Search Report issued Aug. 9, 2011 in International (PCT) Application No. PCT/JP2011/062385.

Mazza, "Stereospecific, Semi-automated, N.C.A. Syntheses of *cis*-4-[$^{18}$F]fluoro-L-proline and *trans*-4-[$^{18}$F]fluoro-L-proline", Journal of Labelled Compounds and Radiopharmaceuticals, vol. 43, pp. 1047-1058, 2000.

"Selective Fluorination of Hydroxy Amines and Hydroxy Amino Acids with Sulfur Tetrafluoride in Liquid Hydrogen Fluoride", Journal of Organic Chemistry, 1975, vol. 40, No. 25, pp. 3808-3809.

Kollonitsch et al., "Fluorodehydroxylation, a Novel Method for Synthesis of Fluoroamines and Fluoramino Acids", Synthesis of Fluoroamines and Fluoroamino Acids, Journal of Organic Chemistry, 1979, vol. 44, No. 5, pp. 771-777.

"2- or 4-Nitrobenzenesulfonamide (Nosyl-NR$_2$ or Ns-NR$_2$): Formulation", Protective Groups in Organic Synthesis, third edition, 1991, pp. 609-610.

Gourdel-Martin et al., "Stereospecific Synthesis of (*Z,E*)-Dienes. An Experimental Verification of Houk's Group Theoretical Predictions for Nitrogen Substituents", Tetrahedron Letters, vol. 37, No. 43, 1996, pp. 7744-7745.

Kato et al., Concise synthesis of glyconoamidines as affinity ligands for the purification of β-glucosidase involved in control of some biological events including plant leaf movement, Tetrahedron Letters, vol. 46, 2005, pp. 4865-4869.

Alvernhe et al., "Fluorination of Amino-alcohols and Hydroxyaziridines by Olah's Reagent", J. Chem. Research, 1983, pp. 246-247.

* cited by examiner

*Primary Examiner* — Jason M Nolan
*Assistant Examiner* — Po-Chih Chen
(74) *Attorney, Agent, or Firm* — Wenderoth, Lind & Ponack, L.L.P.

(57) ABSTRACT

An inexpensive and industrially advantageous method for producing optically active syn-3-(N-substituted-aminomethyl)-4-fluoropyrrolidine which may be an intermediate for producing pharmaceuticals is provided. The present invention relates a method for producing a syn-1-protected-4-fluoro-3-(N-substituted-N-nitrobenzenesulfonyl)pyrrolidine derivative or it's enantiomer, or their salts comprising the process of fluorinating a compound represented by the general formula (6) (in the formula, PG$^1$ represents a protecting group for an amino group, R$^1$ represents a C1 to C6 alkyl group which may be substituted or a C3 to C8 cycloalkyl group which may be substituted, and Ns represents a 2-nitrobenzenesulfonyl group or a 4-nitrobenzenesulfonyl group) or it's enantiomer using a nucleophilic fluorinating agent and an organic base having an amidine or guanidine structure.

(6)

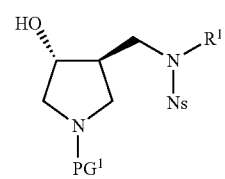

19 Claims, No Drawings

METHOD FOR PRODUCING 3-SUBSTITUTED-4-FLUOROPYRROLIDINE DERIVATIVE

TECHNICAL FIELD

The present invention relates to a novel method for producing optically active form of 3-(N-substituted-aminomethyl)-4-fluoropyrrolidine which is an intermediate useful for producing a 7-(3-(N-substituted-aminomethyl)-4-fluoropyrrolidinyl)quinolone carboxylic acid derivative which, not only, is safe and shows potent antibacterial activity, but also, is effective to resistant bacteria on which conventional antibacterial agents hardly show their effects.

BACKGROUND ART

Patent Documents 1 and 2 disclose a 10-(3-cyclopropylaminomethyl-4-substituted-1-pyrrolidinyl)pyridobenzoxazine carboxylic acid derivative and a 7-(3-cyclopropylaminomethyl-4-substituted-1-pyrrolidinyl)quinolone carboxylic acid derivative as antibacterial agents which show excellent antibacterial activities on resistant bacteria and are highly safe.

Patent Documents 1 and 2 disclose a method for producing (3R,4S)-3-cyclopropylaminomethyl-4-fluoropyrrolidine which is a useful intermediate, but, the synthetic pathway thereof requires nine steps from N-methoxymethyl-N-(trimethylsilylmethyl)benzylamine as a starting material, through a fluorination of 3-azidomethyl-4-hydroxypyrrolidine, to a synthesis of (3R,4S)-3-cyclopropylaminomethyl-4-fluoropyrrolidine.

Patent Documents 3 and 4 also disclose improved methods for preparation of (3R,4S)-3-cyclopropylaminomethyl-4-fluoropyrrolidine.

The method disclosed in Patent Document 3 is a synthesis method in which a fluorinating agent is allowed to react with a 3-bromomethyl-4-hydroxypyrrolidine derivative, and which is led to a 3-bromomethyl-4-fluoropyrrolidine derivative, and then, a cyclopropylamino group is introduced. However, in the method disclosed in Patent Document 3, all intermediates are oily products and are difficult to purify.

In Patent Document 4, a synthesis method for (3R,4S)-3-cyclopropylaminomethyl-4-fluoropyrrolidine using asymmetric hydrogenation is disclosed. In Patent Document 4, introduction of a fluorine group is carried out on a 1-protected-3-(N-protected-N-cyclopropyl)aminomethyl-4-hydroxypyrrolidine derivative using perfluoro-1-octanesulfonyl fluoride. In this case, an aralkyl group such as a benzyl group, an aralkoxycarbonyl group such as a benzyloxycarbonyl group, or an alkoxycarbonyl group such as a tert-butyloxycarbonyl group is used as a protecting group for a cyclopropylamino group.

That is, in Patent Document 4, a fluorination of a 1-protected-3-(N-protected-N-cyclopropyl)aminomethyl-4-hydroxypyrrolidine derivative shown in following scheme 1 is shown as the synthesis method for syn-3-(N-substituted-aminomethyl)-4-fluoropyrrolidines.

Scheme 1

[Chem. 1]

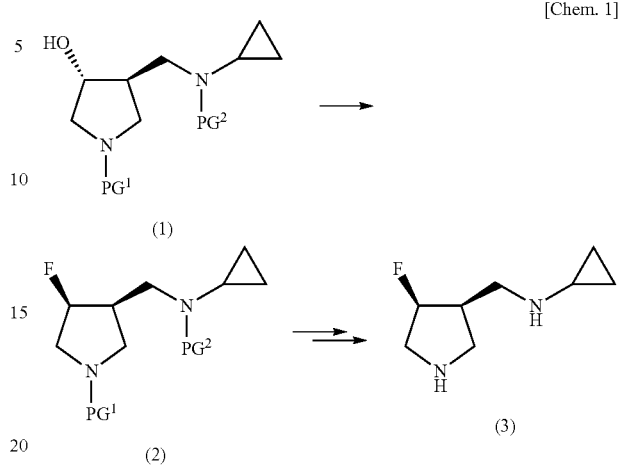

In general formulae (1) and (2), $PG^1$ represents a protecting group for an amino group, $PG^2$ represents an aralkyl group, an aralkoxycarbonyl group, an alkoxycarbonyl group, or an acyl group.

Meanwhile, a method for producing a fluoroamine from an amino alcohol is classified into a method in which after an amino group is protected once, a hydroxyl group is fluorinated and a protecting group for the amino group is deprotected, and a method in which a hydroxyl group is directly fluorinated with an amino group being unprotected.

As the method in which after an amino group is protected once, a hydroxyl group is fluorinated and the amino group is deprotected, examples in which a fluorination reaction is carried out with protecting the amino group with an alkoxycarbonyl group such as a tert-butyloxycarbonyl group (Patent Document 5 and Non-Patent Documents 1 and 2). In addition, Non-Patent Document 6 discloses a fluorination of a N-(2-nitrobenzenesulfonyl)amino alcohol derivative of which an amino group is protected with a 2-nitrobenzenesulfonyl group.

As the prior art in which a fluorination of a hydroxyl group is carried out with an amino group of an amino alcohol being unprotected, a method in which a hydrogen fluoride-pyridine complex is used (Non-Patent Document 3), a method in which a sulfur tetrafluoride derivative is used (Patent Document 6), and a method in which sulfur tetrafluoride and liquid hydrogen fluoride are used (Non-Patent Documents 4 and 5) have been reported.

In the method of Non-Patent Document 3, the yield is relatively satisfactory, however, there is a problem that it takes several days to complete the reaction. In addition, in Patent Document 6, an N-benzyl-N-(2-hydroxyethyl)amine derivative is converted to an N-benzyl-N-(2-fluoroethyl)amine derivative using DAST which is a sulfur tetrafluoride derivative, however, a yield thereof is as low as 17%.

In Non-Patent Documents 4 and 5, a fluorinated amine is obtained from reacting sulfur tetrafluoride in liquid hydrogen fluoride at −78° C., however, a rearrangement of the fluorinated position occurs. That is, when 3-hydroxypiperidine is used, the yield of 3-fluoropiperidine which is the target compound, is reduced since 4-fluoropiperidine which is a positional isomer is formed.

PRIOR ART

Patent Document

[Patent Document 1] International Publication 2003/078439
[Patent Document 2] International Publication 2005/026147
[Patent Document 3] Japanese Patent Publication 2005/239617
[Patent Document 4] International Publication 2007/102567
[Patent Document 5] International Publication 2005/075426
[Patent Document 6] International Publication 2006/13048

Non-Patent Document

[Non-Patent Document 1] Journal of Labelled Compounds & Radiopharmaceuticals, (2000), 43(10), 1047-1058.
[Non-Patent Document 2] Tetrahedron Letters, (1996), 37(43), 7743-7744.
[Non-Patent Document 3] J. Chem. Res., 246, 1983.
[Non-Patent Document 4] Journal of Organic Chemistry, (1979), 44(5), 771-777.
[Non-Patent Document 5] Journal of Organic Chemistry, (1975), 40(25), 3808-3809.
[Non-Patent Document 6] Tetrahedron Letters, (2005), 46, 4865-4869.

SUMMARY OF INVENTION

Problems to Be Solved by the Invention

The inventors of the present invention carried out investigations regarding the synthesis of optically active syn-3-(N-substituted-aminomethyl)-4-fluoropyrrolidine, and found that in the fluorination conditions using conventional methods, a 3,4-elimination compound (4) represented by following the general formula (4) or a 4,5-elimination compound (5) represented by following the general formula (5) is formed as a byproduct in addition to a target fluorinated compound [for example, a compound represented by formula (2) in scheme 1], therefore, the produced amount of the target fluorinated compound (2) is reduced.

In addition, it was found that the 3,4-elimination compound (4) or the 4,5-elimination compound (5) is difficult to be separated from the target fluorinated compound, and the yield of the target fluorinated compound is reduced due to increased purification operations. Therefore, an object of the present invention is to provide a novel synthesis method for an optically active syn-3-(N-substituted-aminomethyl)-4-fluoropyrrolidine with industrial advantages such that the formation of the 3,4-elimination compound (4) or the 4,5-elimination compound (5) is suppressed.

[Chem. 2]

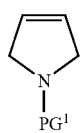

(4)

[Chem. 3]

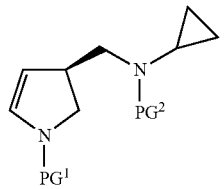

(5)

In the general formula (4), $PG^1$ represents a protecting group for an amino group.

In the general formula (5), $PG^1$ represents a protecting group for an amino group, and $PG^2$ represents an aralkyl group, an aralkoxycarbonyl group, an alkoxycarbonyl group, or an acyl group.

Means for Solving the Problems

To solve the above problems, the present inventors have conducted extensive researches on processes of a novel synthesis method for optically active syn-3-(N-substituted-aminomethyl)-4-fluoropyrrolidine.

As a result, the inventors found that, when a nitrobenzenesulfonyl group is used as a protecting group on an N-substituted-amino group [$PG^2$ in the general formula (1)], the 3,4-elimination compound (4), which is formed when other protecting groups were used is not formed. In addition, it was found that, by adjusting the reaction temperature or the amount of a solvent, the formation of the 4,5-elimination compound (5) may also be suppressed.

That is, the inventors found that, by fluorinating optically active anti-1-protected-3-(N-substituted-N-nitrobenzenesulfonylaminomethyl)-4-hydroxypyrrolidine using a fluorinating agent such as a perfluoroalkanesulfonyl fluoride, a highly pure optically active syn-1-protected-3-(N-substituted-N-nitrobenzenesulfonylaminomethyl)-4-fluoropyrrolidine derivative may be obtained in a high yield.

Further, by reacting the obtained optically active syn-1-protected-3-(N-substituted-N-nitrobenzenesulfonylaminomethyl)-4-fluoropyrrolidine derivative with a thiol compound, an inexpensive and industrially advantageous method for producing optically active syn-1-protected-3-(N-substituted-aminomethyl)-4-fluoropyrrolidine was found, and therefore the present invention was completed.

That is, the present invention includes the following invention.

1. A method for producing a compound represented by the general formula (7) or it's enantiomer, or their salts, comprising step 1:

(Step 1) a process of fluorinating a compound represented by the general formula (6) or it's enantiomer using a nucleophilic fluorinating agent and an organic base having an amidine or guanidine structure,

[Chem. 4]

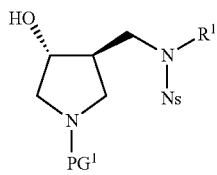

(6)

[wherein, in the general formula (6), PG¹ represents a protecting group for an amino group, R¹ represents a C1 to C6 alkyl group which may be substituted or a C3 to C8 cycloalkyl group which may be substituted, and Ns represents a 2-nitrobenzenesulfonyl group or a 4-nitrobenzenesulfonyl group],

[Chem. 5]

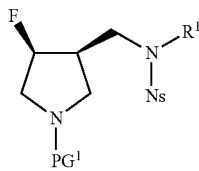

(7)

[wherein, in the general formula (7), PG¹ represents a protecting group for an amino group, R¹ represents a C1 to C6 alkyl group which may be substituted or a C3 to C8 cycloalkyl group which may be substituted, and Ns represents a 2-nitrobenzenesulfonyl group or a 4-nitrobenzenesulfonyl group].

2. A method for producing a compound represented by the general formula (8) or it's enantiomer, or their salts, comprising step1 and step 2:

(Step 1) a process of fluorinating a compound represented by the general formula (6) or it's enantiomer using a nucleophilic fluorinating agent and an organic base having an amidine or guanidine structure; and (Step 2) a process of deprotecting a protecting group on the amino group of the compound represented by the general formula (7) or it's enantiomer, or their salts obtained in step 1 using a thiol compound and a base,

[Chem. 6]

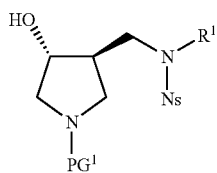

(6)

[wherein, in the general formula (6), PG¹ represents a protecting group for an amino group, R¹ represents a C1 to C6 alkyl group which may be substituted or a C3 to C8 cycloalkyl group which may be substituted, and Ns represents a 2-nitrobenzenesulfonyl group or a 4-nitrobenzenesulfonyl group],

[Chem. 7]

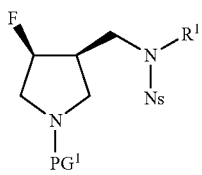

(7)

[wherein, in the general formula (7), PG¹ represents a protecting group for an amino group, R¹ represents a C1 to C6 alkyl group which may be substituted or a C3 to C8 cycloalkyl group which may be substituted, and Ns represents a 2-nitrobenzenesulfonyl group or a 4-nitrobenzenesulfonyl group],

[Chem. 8]

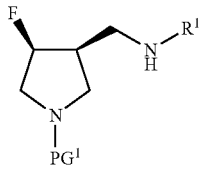

(8)

[wherein in the general formula (8), PG¹ represents a protecting group for an amino group, R¹ represents a C1 to C6 alkyl group which may be substituted or a C3 to C8 cycloalkyl group which may be substituted].

3. The production method described in 1 or 2 above, wherein, in step 1, a perfluoroalkanesulfonyl fluoride is used as the nucleophilic fluorinating agent.

4. The production method described in 3 above, wherein the perfluoroalkanesulfonyl fluoride is nonafluorobutane-1-sulfonyl fluoride.

5. The production method described in any one of 1 to 4 above, wherein, in step 1, a reaction temperature is 10° C. or less.

6. The production method described in any one of 1 to 5 above, wherein, in step 1, a solvent is used 15- to 25-fold amount of the compound represented by the general formula (6) or it's enantiomer.

7. The production method described in any one of 1 to 6 above, wherein, in step 1, tetramethylguanidine, 1,8-diazabicyclo[5.4.0]undec-7-ene, or 1,5-diazabicyclo[4.3.0]non-5-ene is used as the organic base.

8. The production method described in any one of 2 to 7 above, wherein, in step 2, the thiol compound is thioglycolic acid, a C1 to C24 alkylthiol or benzenethiol which may be substituted.

9. The production method described in any one of 2 to 8 above, wherein, in step 2, the base is an alkali metal hydroxide, an alkali metal carbonate, or an organic base having an amidine or guanidine structure.

10. The production method described in 8 or 9 above, wherein, in step 2, the thiol compound is the thioglycolic acid or the C1 to C24 alkylthiol, and the base is the alkali metal hydroxide.

11. The production method described in 10 above, wherein the C1 to C24 alkylthiol is 1-dodecanethiol, and the alkali metal hydroxide is lithium hydroxide.

12. The production method described in any one of 8 to 11 above, wherein, in step 2, N,N-dimethylformamide, N-methylpyrrolidone or N,N-dimethylacetamide is used as a reaction solvent.

13. The production method described in 12 above, wherein, in step 2, the N,N-dimethylformamide is used as the reaction solvent.

14. The production method described in 8 or 9 above, wherein, in step 2, the thiol compound is the benzenethiol which may be substituted, and the base is the alkali metal carbonate.

15. The production method described in 14 above, wherein the benzenethiol which may be substituted is 4-tert-butylbenzenethiol, and the alkali metal carbonate is potassium carbonate or cesium carbonate.

16. The production method described in 14 or 15 above, wherein, in step 2, a lower alcohol, an ether solvent, a nitrile solvent, or a mixed solvent of these is used as the reaction solvent.

17. The production method described in 16 above, wherein a mixed solvent of the lower alcohol and the ether solvent is used as the reaction solvent.

18. The production method described in 17 above, wherein the lower alcohol is ethanol or 2-propanol, and the ether solvent is tetrahydrofuran.

Effects of the Invention

According to the present invention, in the fluorination reaction of a compound represented by the general formula (6) or it's enantiomer, a fluorination reaction without forming the 3,4-elimination compound (4) as a byproduct and also suppressing the formation of the 4,5-elimination compound (5) as a byproduct may be carried out. As a result, production of highly pure compound represented by the general formula (7) or it's enantiomer in high yield is possible. Furthermore, by deprotecting the nitrobenzenesulfonyl group of the compound represented by the general foimula (7) or it's enantiomer, a compound represented by the general formula (8) or it's enantiomer may be produced in large quantities at low cost. That is, the present invention may provide an industrially advantageous method for producing high-quality optically active syn-3-(N-substituted-aminomethyl)-4-fluoropyrrolidine or their salts useful as intermediates for producing pharmaceuticals at low cost.

EMBODIMENTS FOR CARRYING OUT THE INVENTION

Hereinafter, the present invention will be described in detail.

The present invention provides a method for producing a compound represented by following the general formula (7) or it's enantiomer, or their salts including following step 1.
(Step 1) A process of fluorinating a compound represented by following the general formula (6) or it's enantiomer using a nucleophilic fluorinating agent and an organic base having an amidine or guanidine structure

[Chem. 9]

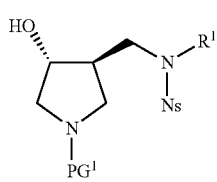
(6)

In the general formula (6), $PG^1$ represents a protecting group for an amino group, $R^1$ represents a C1 to C6 alkyl group which may be substituted, or a C3 to C8 cycloalkyl group which may be substituted, and Ns represents a 2-nitrobenzenesulfonyl group or a 4-nitrobenzenesulfonyl group.

[Chem. 10]

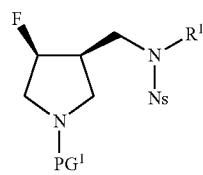
(7)

In the general formula (7), $PG^1$ represents a protecting group for an amino group, $R^1$ represents a C1 to C6 alkyl group which may be substituted, or a C3 to C8 cycloalkyl group which may be substituted, and Ns represents a 2-nitrobenzenesulfonyl group or a 4-nitrobenzenesulfonyl group.

In addition, the present invention provides a method for producing a compound represented by following the general formula (8) or it's enantiomer, or their salts including following step 1 and step 2.
(Step 1) A process of fluorinating a compound represented by the general formula (6) or it's enantiomer using a nucleophilic fluorinating agent and an organic base having an amidine or guanidine structure
(Step 2) A process of deprotecting the protecting group on the amino group of the compound represented by the general formula (7) or it's enantiomer, or their salts obtained from step 1 using a thiol compound and a base

[Chem. 11]

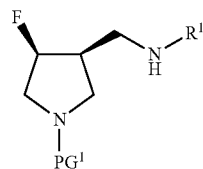
(8)

In the general formula (8), $PG^1$ represents a protecting group for an amino group, $R^1$ represents a C1 to C6 alkyl group which may be substituted, or a C3 to C8 cycloalkyl group which may be substituted.

In general formulae (6) to (8), the "protecting group for an amino group" is not particularly limited as long as the protecting group is commonly known as a protecting group for an amino group, and may include, for example, an aralkyl group such as benzyl group or a p-methoxybenzyl group, an alkoxycarbonyl group such as a methoxycarbonyl group, an ethoxycarbonyl group, a propyloxycarbonyl group, an isopropyloxycarbonyl group, a butyloxycarbonyl group, an isobutyloxycarbonyl group or a tert-butyloxycarbonyl group, an aralkoxycarbonyl group such as a benzyloxycarbonyl group, a p-methoxybenzyloxycarbonyl group or a p-nitrobenzyloxycarbonyl group, a 1-(alkoxy)alkyl group such as a methoxymethyl group, a methoxyethoxymethyl group, a 1-(ethoxy)ethyl group or a methoxyisopropyl group, an acyl group such as an acetyl group, a trifluoroacetyl group, a propionyl group, a butyryl group, a pivaloyl group, a benzoyl group or a methylbenzoyl group, or the like.

Among these, particularly, an aralkoxycarbonyl group or an alkoxycarbonyl group is preferable, an aralkoxycarbonyl group, a methoxycarbonyl group, an ethoxycarbonyl group or a tert-butyloxycarbonyl group is more preferable, an aralkoxycarbonyl group is even more preferable, and a benzyloxycarbonyl group is particularly preferable.

In general formulae (6) to (8), the "C1 to C6 alkyl group which may be substituted" means a C1 to C6 alkyl group which may have one to five substituents selected from the group consisting of a halogen atom, a hydroxyl group, a cyano group, a C1 to C6 alkoxy group, a C3 to C8 cycloalkyl group, an aryloxy group which may be substituted, a C1 to C6 allcylcarbonyl group, a C1 to C6 alkoxycarbonyl group, a C1 to C6 alkylthio group, an amino group, a mono- or di-substituted C1 to C6 alkylamino group, a C4 to C9 cyclic amino group which may include one to three heteroatoms, a formylamino group, a C1 to C6 alkylcarbonylamino group, a C1 to C6 alkoxycarbonylamino group, a C1 to C6 alkylsulfonylamino group and an arylsulfonylamino group which may be substituted.

In general formulae (6) to (8), the "C3 to C8 cycloalkyl group which may be substituted" means a C3 to C8 cycloalkyl group which may have one to five substituents selected from the group consisting of a halogen atom, a hydroxyl group, a cyano group, a C1 to C6 alkoxy group, an aryloxy group which may be substituted, a C1 to C6 alkylcarbonyl group, a C1 to C6 alkoxycarbonyl group, a C1 to C6 alkylthio group, an amino group, a mono- or di-substituted C1 to C6 alkylamino group, a C4 to C9 cyclic amino group which may include one to three heteroatoms, a formylamino group, a C1 to C6 alkylcarbonylamino group, a C1 to C6 alkoxycarbonylamino group, a C1 to C6 alkylsulfonylamino group and an arylsulfonylamino group which may be substituted.

The "C3 to C8 cycloalkyl group" means, for example, an alkyl group having a cycloalkyl ring, and may include, for example, a cyclopropyl group, a cyclobutyl group, a cyclopentyl group, a cyclohexyl group, a cycloheptyl group, a cyclooctyl group, or the like. Among these, a cyclopropyl group is preferable.

The "aryloxy group which may be substituted" means an aryloxy group which may have one to five substituents selected from a group consisting of a halogen atom, a hydroxyl group, a cyano group, a nitro group, a C1 to C6 alkyl group, a C1 to C6 alkoxy group and a C1 to C6 alkylthio group.

Examples of the "aryloxy group" may include a phenoxy group, a naphthyloxy group, or the like.

Examples of the "C1 to C6 alkylcarbonyl group" may include a formyl group, an acetyl group, a propionyl group, a butyryl group, an isobutyryl group, a valeryl group, an isovaleryl group, or the like.

Examples of the "C1 to C6 alkoxycarbonyl group" may include a methoxycarbonyl group, an ethoxycarbonyl group, a tert-butoxycarbonyl group, or the like.

The "mono- or di-substituted C1 to C6 alkylamino group" means a C1 to C6 alkylamino group which may have one to two substituents selected from the group consisting of a halogen atom, a hydroxyl group, a cyano group, a C1 to C6 alkoxy group, a C1 to C6 alkylthio group, an amino group, a C4 to C9 cyclic amino group which may include one to three heteroatoms, a formylamino group, a C1 to C6 alkylcarbonylamino group, a C1 to C6 alkylsulfonylamino group, an arylsulfonylamino group which may be substituted, or the like.

Examples of the "C1 to C6 alkylamino group" may include a methylamino group, an ethylamino group, an n-propylamino group, an n-butylamino group, a sec-butylamino group, an n-pentylamino group, an n-hexyl amino group, or the like.

The "C4 to C9 cyclic amino group" means a cyclic amino group which contains one or more nitrogen atoms in the ring and in which an oxygen atom or a sulfur atom may also be present in the ring. Examples of the C4 to C9 cyclic amino group may include an aziridyl group, a pyrrolidyl group, a piperidyl group, a morpholyl group, an oxazolyl group, an azabicycloheptyl group, an azabicyclooctyl group, or the like.

Examples of the "C1 to C6 alkylcarbonylamino group" may include an acetylamino group, a propionylamino group, a butyrylamino group, or the like.

Examples of the "C1 to C6 alkoxycarbonylamino group" may include a methoxycarbonylamino group, an ethoxycarbonylamino group, a tert-butoxycarbonylamino group, a hexyloxycarbonylamino group, or the like.

Examples of the "C1 to C6 alkylsulfonylamino group" may include a methylsulfonylamino group, an ethylsulfonylamino group, or the like.

The "arylsulfonylamino group which may be substituted" means an arylsulfonylamino group which may have one to five substituents selected from the group consisting of a halogen atom, a hydroxyl group, a cyano group, a nitro group, a C1 to C6 alkyl group, a C1 to C6 alkoxy group and a C1 to C6 alkylthio group.

Examples of the "arylsulfonylamino group" may include a phenylsulfonylamino group, a 4-methylphenylsulfonylamino group, a naphthylsulfonylamino group, or the like.

The "C1 to C6 alkyl group" means a straight chain or branched lower alkyl group. Examples of the C1 to C6 alkyl group may include a methyl group, an ethyl group, a propyl group, a 1-methylethyl group, a 1-methylpropyl group, a 2-methylpropan-1-yl group, a tert-butyl group, a 1-ethylpropyl group, a 2-ethylpropyl group, a butyl group, a hexyl group, or the like. Among these, an ethyl group or a tert-butyl group is preferable.

Examples of the "C1 to C6 alkoxy group" may include a methoxy group, an ethoxy group, a butoxy group, a hexyloxy group, or the like.

Examples of the "C1 to C6 alkylthio group" may include a methylthio group, an ethylthio group, a propylthio group, an isopropylthio group, or the like.

The Ns group in general formulae (6) and (7) is a nitrobenzenesulfonyl group, and may include, for example, a 2-nitrobenzenesulfonyl group or a 4-nitrobenzenesulfonyl group. In the present invention, a fluorination reaction without forming the 3,4-elimination compound (4) as a byproduct and also suppressing the formation of the 4,5-elimination compound (5) as a byproduct may be carried out by protecting the protecting group on the N-substituted-amino group with the Ns group in the general formula (6).

The production method for the present invention is shown in scheme 2.

Scheme 2

[Chem. 12]

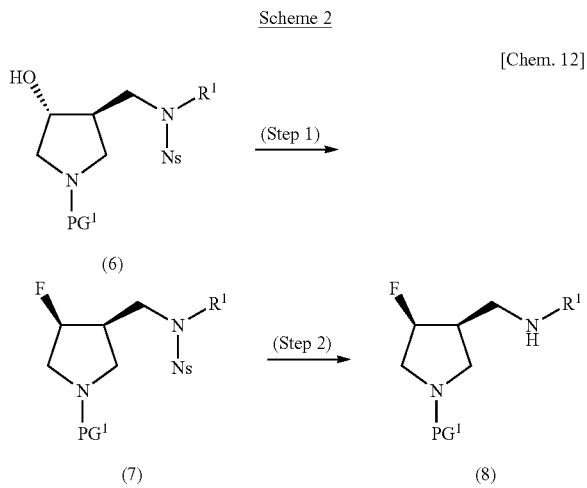

In scheme 2, $PG^1$ and $R^1$ in formulae (6) to (8) have the same meanings as described above.

I. Step 1

Step 1 is a process of fluorinating the compound represented by the general formula (6) or it's enantiomer using a nucleophilic fluorinating agent and an organic base having an amidine or guanidine structure, and thus obtaining the compound represented by the general formula (7) or it's enantiomer, or their salts by converting a hydroxyl group of the compound represented by the general formula (6) or it's enantiomer to a fluoro group.

The "nucleophilic fluorinating agent" is not particularly limited as long as it is a nucleophilic fluorinating agent and may include, for example, a perfluoroalkanesulfonyl fluoride, a sulfur trifluoride derivative, a fluoroalkylamine derivative, 2,2-difluoro-1,3-dimethylimidazolidine (DFI) or a sulfuryl fluoride. Among these, a perfluoroalkanesulfonyl fluoride is preferable.

Examples of the perfluoroalkanesulfonyl fluoride may include trifluoromethanesulfonyl fluoride, nonafluorobutane-1-sulfonyl fluoride, tridecafluorohexane-1-sulfonyl fluoride, heptadecafluorooctane-1-sulfonyl fluoride, tricosafluorododecane-1-sulfonyl fluoride, or the like.

Among these, nonafluorobutane-1-sulfonyl fluoride, tridecafluorohexane-1-sulfonyl fluoride or heptadecafluorooctane-1-sulfonyl fluoride is preferable, and nonafluorobutane-1-sulfonyl fluoride is more preferable. In addition, the perfluoroalkanesulfonyl fluoride is used more compared to other fluorinating agents due to its availability at a relatively low cost.

Examples of the sulfur trifluoride derivative may include (dimethylamino)sulfur trifluoride (Methyl DAST), (diethylamino)sulfur trifluoride (DAST), morpholino sulfur trifluoride (Morpho-DAST), bis(2-methoxyethyl)aminosulfur trifluoride (Deoxo-Fluor), or the like.

Examples of the fluoroalkylamine derivative may include Yarovenko's reagent (2-chloro-1,1,2-trifluoroethyldiethylamine), Ishikawa's reagent (1,1,2,3,3,3-hexafluoropropyldiethylamine), 1,1,2,2-tetrafluoroethyl-N,N-dimethylamine (TFEDMA), N,N-diethyl-α,α-difluoro-3-methylbenzylamine (DFMBA), or the like.

As the amount of the fluorinating agent, typically, 1 to 5 equivalents is preferably used, 1 to 2 equivalents is more preferably used, and 1 to 1.6 equivalents is even more preferably used with regard to the compound represented by the general formula (6).

Examples of the organic base having an amidine or guanidine structure may include a base having an amidine structure such as 1,8-diazabicyclo[5.4.0]undec-7-ene (DBU), 1,5-diazabicyclo[4.3.0]non-5-ene (DBN), pyrimidine, 1-methylimidazole or 3,4,6,7,8,9-hexahydro-2H-pyrido[1,2-a]pyrimidin, or an organic base having a guanidine structure such as 1,1,3,3-tetramethylguanidine (TMG) or guanidino phosphazene. Among these, DBU, DBN or TMG is preferable, and DBU is more preferable.

In step 1, the amount of the organic base having an amidine or guanidine structure used is preferably 1 to 5 equivalents, more preferably 1 to 2 equivalents, and even more preferably 1 to 1.6 equivalents with regard to the compound represented by the general formula (6).

In step 1, the reaction temperature is preferably in the range of −78° C. to 60° C., more preferably 25° C. or less, and even more preferably 10° C. or less. By lowering the reaction temperature, formation of the 4,5-elimination compound represented by the general formula (9) may be suppressed.

In addition, in step 1, the reaction time may be appropriately adjusted depending on the reaction temperature and the amount of the reagent.

The reaction solvent used in step 1 is not particularly limited as long as it is a reaction solvent which is stable under the conditions of the reaction and is inert, therefore not interfering with the reaction. Examples of such a solvent may include hydrocarbons such as hexane, cyclohexane or heptane, aromatic hydrocarbons such as benzene, toluene or xylene, ethers such as 1,2-dimethoxyethane (DME), tetrahydrofuran (THF), diisopropyl ether, 2-methyltetrahydrofuran, tetrahydropyran, diglyme or cyclopentyl methyl ether, esters such as methyl acetate, ethyl acetate, isopropyl acetate or butyl acetate, nitriles such as acetonitrile or propionitrile, or halogenated hydrocarbons such as dichloromethane, chloroform, 1,2-dichloroethane or 1,1,1,3,3-pentafluorobutane.

These solvents are appropriately selected while taking into consideration the easiness of the occurrence of the reaction and are used either alone or as a mixed solvent. In addition, in some cases, these solvents are used as a non-aqueous solvent using an appropriate dehydrating agent or a drying agent. In step 1, toluene, 1,2-dimethoxyethane (DME) or dichloromethane is preferable, and toluene is more preferable.

In step 1, as the amount of the solvent used, preferably 5- to 45-fold amount, more preferably 10- to 30-fold amount, and particularly preferably 15- to 25-fold amount of the solvent with regard to the general formula (6) are used. By increasing the amount of the solvent used, formation of the 4,5-elimination compound (9) represented by following the general formula (9) may be suppressed. The fluorination reaction is less likely to proceed if an excess amount of solvent is used, therefore, using an appropriate amount of solvent is preferable.

[Chem. 13]

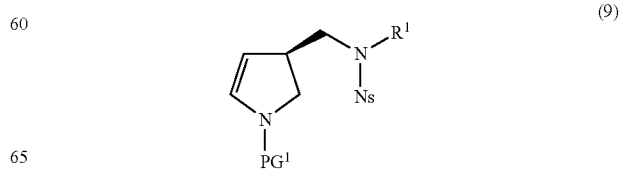

(9)

In the general formula (9), $PG^1$ and $R^1$ have the same meanings as described above.

The "-fold amount" described in the present specification means a volume (mL) of the solvent used with regard to a weight (g) of the compound used in the reaction and is calculated from the following formula.

Fold amount(v/w)=(volume of solvent)(mL)/(compound used in reaction)(g)

After the reaction of step 1 is complete, the compound represented by the general formula (7) or it's enantiomer, or their salts, may be purified and isolated as desired by using normal methods of separation (for example, extraction, recrystallization, chromatography or the like).

II. Step 2

Step 2 is a process of deprotecting the Ns group which is a protecting group on the amino group of the compound represented by the general formula (7) or it's enantiomer, or their salts obtained in step 1 using a thiol compound and a base, and obtaining the compound represented by the general formula (8) or it's enantiomer, or their salts.

In step 2, a thiol compound is used as a deprotection reagent. Examples of the thiol compound may include thioglycolic acid, a C1 to C24 alkylthiol, benzenethiol which may be substituted or an aralkylthiol which may be substituted.

Examples of the C1 to C24 alkylthiol may include ethanethiol, 1-butanethiol, 1-hexanethiol, 1-dodecanethiol, 1-tetradecanethiol, 2-methyl-1-tridecanethiol, 1-icosanethiol, 1-tetracosanethiol, 2-propanethiol, 2-butanethiol, 3-pentanethiol, 2-decanethiol, 3-decanethiol, 4-decanethiol, 5-decanethiol, 2-hexadecanethiol, 5-hexadecanethiol, 8-octadecanethiol, or the like.

The benzenethiol which may be substituted means benzenethiol which may have one to two substituents selected from the group consisting of hydrogen, a halogen atom, a C1 to C12 alkyl group, a carboxyl group, a C1 to C6 alkoxy group, a C1 to C6 alkylamino group, a trialkylsilyl group, or the like.

The "C1 to C12 alkyl group" means a straight chain or branched lower alkyl group. Examples of the C1 to C12 alkyl group may include a methyl group, an ethyl group, a propyl group, a 1-methylethyl group, a 1-methylpropyl group, a 2-methylpropan-1-yl group, a tert-butyl group, a 1-ethylpropyl group, a 2-ethylpropyl group, a butyl group, a pentyl group, a hexyl group, an 2-ethylbutyl group, a 4-methylpentyl group, a heptyl group, a 1-methylhexyl group, an octyl group, a decyl group, an undecyl group, a dodecyl group, or the like. Among these, a tert-butyl group or a dodecyl group is preferable, and a tert-butyl group is more preferable.

Examples of the "C1 to C6 alkoxy group" may include a methoxy group, an ethoxy group, a butoxy group, a hexyloxy group, or the like.

Examples of the "C1 to C6 alkylamino group" may include a methylamino group, an ethylamino group, an n-propylamino group, an n-butylamino group, a sec-butylamino group, an n-pentylamino group, an n-hexyl amino group, or the like.

The "trialkylsilyl group" is a silyl group substituted with three identical or different alkyl groups. Examples of the trialkylsilyl group may include a trimethylsilyl group, a tert-butyldimethylsilyl group, or the like.

Examples of the benzenethiol which may have a substituent may include benzenethiol, dodecylbenzenethiol, 4-tert-butylbenzenethiol, 2-methyl-5-tert-butylbenzenethiol, 2-mercaptobenzoic acid, 4-mercaptobenzoic acid, 4-trimethylsilylbenzenethiol, or the like.

The aralkylthiol which may be substituted means an aralkylthiol which, on the ring, may have one to two substituents selected from the group consisting of hydrogen, a halogen atom, a C1 to C12 alkyl group, a carboxyl group, C1 to C6 alkoxy group, a C1 to C6 alkylamino group, a trialkylsilyl group, or the like.

The "C1 to C12 alkyl group" means a straight chain or branched lower alkyl group. Examples of the C1 to C12 alkyl group may include a methyl group, an ethyl group, a propyl group, a 1-methylethyl group, a 1-methylpropyl group, a 2-methylpropan-1-yl group, a tert-butyl group, a 1-ethylpropyl group, a 2-ethylpropyl group, a butyl group, a pentyl group, a hexyl group, a 2-ethylbutyl group, a 4-methylpentyl group, a heptyl group, a 1-methylhexyl group, an octyl group, a decyl group, an undecyl group, a dodecyl group, or the like.

Examples of the "C1 to C6 alkoxy group" may include a methoxy group, an ethoxy group, a butoxy group, a hexyloxy group, or the like.

Examples of the "C1 to C6 alkylamino group" may include a methylamino group, an ethylamino group, an n-propylamino group, an n-butylamino group, a sec-butylamino group, an n-pentylamino group, an n-hexyl amino group, or the like.

The "trialkylsilyl group" is a silyl group substituted with three identical or different alkyl groups. Examples of the trialkylsilyl group may include a trimethylsilyl group, a tert-butyldimethylsilyl group, or the like.

Examples of the aralkylthiol which may have a substituent may include 4-n-heptylphenylmethanethiol, 4-trimethylsilylphenylmethanethiol, benzylthiol, or the like.

Among these, thioglycolic acid, a C1 to C12 alkylthiol such as 1-dodecanethiol or 2-decanethiol, benzenethiol, benzenethiol substituted with a C1 to C12 alkyl group such as dodecylbenzenethiol, 4-tert-butylbenzenethiol or 2-methyl-5-tert-butylbenzenethiol, or benzenethiol substituted with a carboxyl group such as 2-mercaptobenzoic acid or 4-mercaptobenzoic acid is preferable.

In addition, thioglycolic acid, a C1 to C12 alkylthiol, benzenethiol or benzenethiol which is substituted with a C1 to C12 alkyl group is preferable, a C1 to C12 alkylthiol or benzenethiol substituted with a C1 to C12 alkyl group is more preferable, and 1-dodecanethiol or 4-tert-butylbenzenethiol is particularly preferable.

As the amount of the thiol compound used, typically, 1 to 5 equivalents is preferable, 1 to 3 equivalents is more preferable, and 1 to 2 equivalents is even more preferable with regard to the compound represented by the general formula (7).

In step 2, as the base, any base from organic bases or inorganic bases may be used. The use of the inorganic base is preferable since the compound represented by the general formula (8) is readily separated from the inorganic base used compared to the organic base when the inorganic base is used.

As the organic base, an organic base having an amidine or guanidine structure is preferable. Examples of the organic base having an amidine or guanidine structure may include a base having an amidine structure such as 1,8-diazabicyclo[5.4.0]undec-7-ene (DBU), 1,5-diazabicyclo[4.3.0]non-5-ene (DBN), pyrimidine, 1-methylimidazole or 3,4,6,7,8,9-hexahydro-2H-pyrido[1,2-a]pyrimidine, or an organic base having a guanidine structure such as 1,1,3,3-tetramethylguanidine (TMG) or guanidino phosphazene. Among these, DBU, DBN or TMG is preferable, and DBU is more preferable.

Examples of the inorganic base may include a metal hydroxide, a metal carbonate or a metal hydrogen carbonate. Among the metal hydroxide, the metal carbonate or the metal hydrogen carbonate, an alkali metal hydroxide, an alkali metal carbonate or an alkali metal hydrogen carbonate is preferable, and an alkali metal hydroxide or an alkali metal carbonate is more preferable.

Examples of the metal hydroxide may include lithium hydroxide, sodium hydroxide, potassium hydroxide, rubidium hydroxide, cesium hydroxide, beryllium hydroxide, magnesium hydroxide, calcium hydroxide, strontium hydroxide, barium hydroxide, aluminum hydroxide, or the like. Among these, lithium hydroxide, sodium hydroxide, potassium hydroxide, rubidium hydroxide or cesium hydroxide which is an alkali metal hydroxide is preferable, and lithium hydroxide is more preferable.

Examples of the metal carbonate may include lithium carbonate, sodium carbonate, potassium carbonate, rubidium carbonate, cesium carbonate, beryllium carbonate, magnesium carbonate, calcium carbonate, strontium carbonate or barium carbonate. Among these, cesium carbonate, potassium carbonate, sodium carbonate, rubidium carbonate or lithium carbonate which is an alkali metal carbonate is preferable, cesium carbonate or potassium carbonate is more preferable, and potassium carbonate is even more preferable.

Examples of the metal hydrogen carbonate may include lithium hydrogen carbonate, sodium hydrogen carbonate, potassium hydrogen carbonate, rubidium hydrogen carbonate, cesium hydrogen carbonate, beryllium hydrogen carbonate, magnesium hydrogen carbonate, calcium hydrogen carbonate, strontium hydrogen carbonate or barium hydrogen carbonate. Among these, lithium hydrogen carbonate, sodium hydrogen carbonate, potassium hydrogen carbonate, rubidium hydrogen carbonate or cesium hydrogen carbonate which is an alkali metal hydrogen carbonate is preferable.

In step 2, when thioglycolic acid or a C1 to C24 alkylthiol is used as the thiol compound, combining an alkali metal hydroxide as the base is preferable. As a more preferable combination, the use of lithium hydroxide as a base is preferable when thioglycolic acid or a C1 to C24 alkylthiol is used as the thiol compound. In addition, a combination of 1-dodecanethiol and an alkali metal hydroxide is more preferable, and a combination of 1-dodecanethiol and lithium hydroxide is particularly preferable.

On the other hand, when benzenethiol which may be substituted is used as the thiol compound, combining an alkali metal carbonate as the base is preferable. As a more preferable combination, when 4-tert-butylbenzenethiol is used as the benzenethiol, the use of an alkali metal carbonate as the base is preferable, and potassium carbonate or cesium carbonate is more preferable. Furthermore, a combination of 4-tert-butylbenzenethiol, and potassium carbonate or cesium carbonate is more preferable.

The reaction solvent used in step 2 is not particularly limited as long as it is a reaction solvent which is stable under the conditions of the reaction and is inert, therefore not interfering with the reaction. Examples of such a solvent may include water, a lower alcohol, an ether solvent, an ester solvent, a nitrile solvent, an amide solvent, a sulfoxide solvent, or the like. These solvents are appropriately selected while taking into consideration the easiness of the occurrence of the reaction and are used either alone or as a mixed solvent.

The lower alcohol represents a branched or straight chain aliphatic alcohol having 1 to 4 carbon atoms. Example of the lower alcohol may include methanol, ethanol, 1-propanol, 2-propanol, 1-butanol, isobutanol, tert-butanol, or the like.

Examples of the ether solvent may include an ether solvent such as 1,2-dimethoxyethane (DME), tetrahydrofuran (THF), diisopropyl ether, 2-methyltetrahydrofuran, tetrahydropyran, diglyme or cyclopentyl methyl ether.

Examples of the ester solvent may include methyl acetate, ethyl acetate, isopropyl acetate, butyl acetate, or the like.

Examples of the nitrile solvent may include acetonitrile, propionitrile, or the like.

Examples of the amide solvent may include formamide, N,N-dimethylformamide (DMF), N-methylpyrrolidone, N,N-dimethylacetamide, or the like.

Examples of the sulfoxide solvent may include dimethylsulfoxide, sulfolane, or the like.

If the base used in step 2 is an alkali metal hydroxide, the reaction solvent used is preferably a lower alcohol, a sulfoxide solvent or an amide solvent. In particular, an amide solvent such as N,N-dimethylformamide (DMF), N-methylpyrrolidone, or N,N-dimethylacetamide is more preferable, and N,N-dimethylformamide is even more preferable.

If the base used in step 2 is an alkali metal carbonate, the use of a lower alcohol, an ether solvent, a nitrile solvent, or a mixed solvent of these is preferable. A lower alcohol, tetrahydrofuran, acetonitrile, or a mixed solvent of these is more preferable, a lower alcohol, tetrahydrofuran, or a mixed solvent of these is even more preferable, water, 2-propanol, ethanol, tetrahydrofuran, or a mixed solvent of tetrahydrofuran and water, 2-propanol or ethanol is particularly preferable, and a mixed solvent of ethanol and tetrahydrofuran or a mixed solvent of 2-propanol and tetrahydrofuran is most preferable.

In addition, if the base used in step 2 is an organic base having an amidine or guanidine structure, the use of a nitrile solvent is preferable, and the use of acetonitrile is more preferable.

In step 2, the amount of the solvent used is preferably 1- to 20-fold amount and more preferably 2- to 8-fold amount with regard to the compound represented by the general formula (7).

At the beginning of the reaction of step 2, problems sometimes occur in that solubility of the compound represented by the general formula (7) is low and the stirring is not possible to be carried out, however, by using a suitable solvent, the problem can be avoided.

In step 2, the reaction temperature is preferably in the range from $-78°$ C. to the boiling point of the solvent, more preferably 10 to 80° C., even more preferably 10 to 60° C., and particularly preferably, 20 to 60° C.

In addition, in step 2, the reaction time may be appropriately adjusted depending on the reaction temperature and the amount of the reagent.

In step 2, after the reaction is complete, the compound represented by the general formula (8) or it's enantiomer may be isolated as desired by being purified using normal methods of separation (for example, extraction, recrystallization, chromatography or the like).

III. Removal of Protecting Group

The compound represented by the general formula (8) or it's enantiomer may be converted to a compound represented by following the general formula (10) or it's enantiomer, or their salts by appropriately removing the protecting group ($PG^1$). Such a removal of the protecting group may be carried out by appropriately employing the method described in the literature (Green, T. W.; Wuts, P. G. M. "Protective Groups in Organic Synthesis", $2^{nd}$ Ed., Wiley Interscience Publication, John Wiley & Sons, New York, 1991, p 309 to 348.).

[Chem. 14]

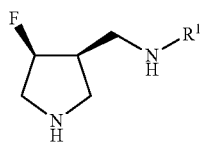

(10)

In the general formula (10), $R^1$ have the same meanings as described above.

III-1. A Case in which Protecting Group is Aralkoxycarbonyl Group or Aralkyl Group For example, if the protecting group (PG) is an aralkoxycarbonyl group such as a benzyloxycarbonyl group or an aralkyl group such as a benzyl group or a p-methoxybenzyl group, the protecting group may be removed by catalytic hydrogenation in the presence of a hydrogen source.

Examples of the catalyst used may include a palladium catalyst such as palladium on carbon, palladium on alumina, palladium black or palladium oxide. Among these, palladium on carbon is preferable.

Examples of the hydrogen source may include hydrogen, formic acid/triethylamine system, formic acid/α-phenethylamine system, formic acid/triphenylamine system, 2-propanol, or the like. Among these, hydrogen is preferable.

As the hydrogen pressure of the reaction, typically, the range from atmospheric pressure to 100 atm is preferable, the range from atmospheric pressure to 10 atm is more preferable, and atmospheric pressure is even more preferable.

In the reaction, typically, it is preferable to use a solvent. Examples of the solvent may include alcohols such as methanol, ethanol, tert-butyl alcohol, ethylene glycol or diethylene glycol, water, ethers such as tetrahydrofuran, cyclopentyl methyl ether, dioxane, dimethoxyethane or diglyme, aromatic hydrocarbons such as benzene, toluene or xylene, hydrocarbons such as hexane, heptane or cyclohexane, or a mixture of these. Among these, alcohols are preferable and ethanol is more preferable.

As the reaction temperature, typically, the range from 0° C. to the boiling point of the solvent used is preferable, and the range from room temperature to the boiling point of the solvent used is more preferable.

In addition, in order to prevent the decomposition of the product, an acid such as sulfuric acid, hydrochloric acid, phosphoric acid, perchloric acid or trifluoroacetic acid, or a base such as ammonia, pyridine, triethylamine, sodium hydroxide or potassium hydroxide may be added. The addition of an acid is preferable and hydrochloric acid is more preferable.

III-2. A Case in which Protecting Group is Aralkoxycarbonyl Group or Alkoxycarbonyl Group In addition, for example, if the protecting group (PG$^1$) is an aralkoxycarbonyl group such as a benzyloxycarbonyl group or an alkoxycarbonyl group such as tert-butoxycarbonyl group, the protecting group may be removed by an organic or inorganic acid.

Examples of the acid which may be used may include an inorganic acid such as hydrochloric acid, sulfuric acid, hydrogen bromide, trifluoromethanesulfonic acid or hydrogen iodide, or an organic acid such as acetic acid, trifluoroacetic acid, trifluoromethanesulfonic acid or p-toluenesulfonic acid. Among these, hydrochloric acid is preferable.

In the reaction, typically, it is preferable to use a solvent. Examples of the solvent may include water, methanol, ethanol, propanol, butanol, acetonitrile, dioxane, dichloromethane, chloroform, N,N-dimethylformamide, dimethylsulfoxide, N-methylpyrrolidone, sulfolane, methyl ethyl ketone, tetrahydropyran, or a mixture of these, and among these, water is preferable.

As the reaction temperature, typically, the range from 0° C. to the boiling point of the solvent used is preferable, and the range from room temperature to the boiling point of the solvent used is more preferable.

EXAMPLES

Next, the present invention will be described using Examples, however, the present invention is not limited to these Examples.

Incidentally, benzyl (3S,4R)-3-(cyclopropylaminomethyl)-4-hydroxypyrrolidine-1-carboxylate hydrochloride used as a raw material in Reference Examples 1 to 4 and benzyl (3S,4R)-3-(N-cyclopropyl-N-benzylaminomethyl)-4-hydroxypyrrolidine-1-carboxylate used as a raw material in Comparative Example 1 may all be produced according to the method disclosed in International Publication 2007/102567.

Reference Example 1

Benzyl (3R,4R)-3-(N-cyclopropyl-N-(2-nitrobenzenesulfonyl)aminomethyl)-4-hydroxypyrrolidine-1-carboxylate A mixture of 120 mL of 1,2-dimethoxyethane and 10.0 mL of water was added to 15.0 g (45.9 mmol) of benzyl (3S,4R)-3-(cyclopropylaminomethyl)-4-hydroxypyrrolidine-1-carboxylate hydrochloride to dissolve the same, and a sodium hydrogen carbonate solution (a solution in which 9.64 g (0.115 mmol) of sodium hydrogen carbonate was dissolved in 140 mL of water) was added at 39 to 40° C. under stirring.

A solution of 12.7 g of 2-nitrobenzenesulfonyl chloride in 30.0 mL of 1,2-dimethoxyethane was added dropwise to the reaction mixture at 41 to 43° C., followed by stirring for 2 hours at 41 to 43° C. The reaction mixture was extracted with 150 mL of tert-butyl methyl ether, and anhydrous magnesium sulfate was added to the organic layer.

The anhydrous magnesium sulfate was separated by filtration and washed with 50.0 mL of tert-butyl methyl ether. The filtrate and the washing were combined and concentrated under reduced pressure to obtain 22.5 g of benzyl (3R,4R)-3-(N-cyclopropyl-N-(2-nitrobenzenesulfonyl)aminomethyl)-4-hydroxypyrrolidine-1-carboxylate as a yellow oil.

$^1$H-NMR (CDCl$_3$, 400 MHz) δ: 0.53-0.77 (4H, m), 3.42 (1H, dd, J=4.4, 19.5 Hz), 2.52-2.67 (2H, m), 3.18-3.26 (2H, m), 3.36 (1H, ddd, J=4.6, 11.2, 11.5 Hz), 3.54 (1H, ddd, J=9.0, 14.6, 23.9 Hz), 3.70-3.83 (2H, m), 4.29-4.39 (1H, m), 5.11-5.17 (2H, m), 7.29-7.39 (5H, m), 7.63-7.66 (1H, m), 7.68-7.76 (2H, m), 8.11-8.17 (1H, m).

HPLC relative purity: 96.6% (RT: 4.74 min), column: Inertsil ODS-3, 4.6 mm×150 mm, pre-column: Inertsil ODS-3, 4.0 mm×10 mm, mobile phase: diluted phosphoric acid (1 in 1,000) (solution A), acetonitrile (solution B), 0 to 20 minutes; solution A:solution B=50:50 (isocratic), detection wavelength: 220 nm, column temperature: 30° C., flow rate: 1.0 mL/min Incidentally, the solution A was prepared by diluting phosphoric acid 1,000 times with distilled water used for HPLC. (The "solution A" in the present specification means an aqueous solution of phosphoric acid prepared in the same way.)

Reference Example 2

Benzyl (3R,4R)-3-(N-cyclopropyl-N-(4-nitrobenzenesulfonyl)aminomethyl)-4-hydroxypyrrolidine-1-carboxylate 8.00 mL of 1,2-dimethoxyethane was added to 1.00 g (3.06 mmol) of benzyl (3S,4R)-3-(cyclopropylaminomethyl)-4-hydroxypyrrolidine-1-carboxylate hydrochloride to suspend the same, and a sodium hydrogen carbonate solution (a solution in which 0.643 g of sodium hydrogen carbonate was dissolved in 10.0 mL of water) was added under stirring.

A solution of 0.848 g (3.83 mmol) of 4-nitrobenzenesulfonyl chloride in 2.00 mL of 1,2-dimethoxyethane was added dropwise to the reaction mixture, followed by stirring for 2 hours at 40 to 45° C. The reaction mixture was extracted with 10.0 mL of tert-butyl methyl ether, the organic layer was separated, and then, anhydrous magnesium sulfate was added thereto.

The anhydrous magnesium sulfate was separated by filtration and washed with 5.00 mL of tert-butyl methyl ether. The filtrate and the washing were combined and concentrated under reduced pressure. The residue was purified by silica gel column chromatography [SiO$_2$, n-hexane/ethyl acetate/acetone=1/2/1 (v/v)] to obtain 1.65 g of benzyl (3R,4R)-3-(N-cyclopropyl-N-(4-nitrobenzenesulfonyl)aminomethyl)-4-hydroxypyrrolidine-1-carboxylate as a colorless oil.

$^1$H-NMR (CDCl$_3$, 400 MHz) δ: 0.73-0.97 (4H, m), 2.05-2.12 (1H, m), 2.24 (1H, dd, J=4.3, 17.4 Hz), 2.56-2.66 (1H, m), 3.02 (1H, ddd, J=7.3, 14.3, 16.5 Hz), 3.17-3.45 (3H, m), 3.67-3.82 (2H, m), 4.25-4.37 (1H, m), 5.14 (2H, s), 7.26-7.39 (5H, m), 8.00-8.04 (2H, m), 8.38 (2H, dd, J=3.1, 8.5 Hz).

HPLC relative purity: 96.2% (RT: 4.77 min), column: Inertsil ODS-3, 4.6 mm×150 mm, pre-column: Inertsil ODS-3, 4.0 mm×10 mm, mobile phase: diluted phosphoric acid (1 in 1,000) (solution A), acetonitrile (solution B), 0 to 20 minutes; solution A:solution B=50:50 (isocratic), detection wavelength: 220 nm, column temperature: 30° C., flow rate: 1.0 mL/min

Reference Example 3

Benzyl (3R,4R)-3-((N-tert-butoxycarbonyl-N-cyclopropyl)aminomethyl)-4-hydroxypyrrolidine-1-carboxylate 10.0 mL of tetrahydrofuran was added to 1.00 g (3.06 mmol) of benzyl (3 S,4R)-3-(cyclopropylaminomethyl)-4-hydroxypyrrolidine-1-carboxylate hydrochloride to suspend the same, and a sodium hydrogen carbonate solution (a solution in which 0.643 g of sodium hydrogen carbonate was dissolved in 10.0 mL of water) was added under stirring.

0.735 g of di-tert-butyl dicarbonate was added dropwise to the reaction mixture, followed by stirring for 2 hours at room temperature. The reaction mixture was extracted with 20.0 mL of ethyl acetate and 20.0 mL of saturated brine, the organic layer was separated, and then, anhydrous magnesium sulfate was added thereto. The anhydrous magnesium sulfate was separated by filtration and washed with 10.0 mL of ethyl acetate.

The filtrate and the washing were combined and concentrated under reduced pressure to obtain 1.21 g of benzyl (3R,4R)-3-((N-tert-butoxycarbonyl-N-cyclopropypaminomethyl)-4-hydroxypyrrolidine-1-carboxylate as a colorless oil.

$^1$H-NMR (CDCl$_3$, 400 MHz) δ: 0.56-0.65 (2H, m), 0.73-0.79 (2H, m), 1.40-1.49 (9H, m), 2.22-2.37 (1H, m), 2.50-2.57 (1H, m), 3.13-3.41 (4H, m), 3.65-3.82 (2H, m), 4.08-4.15 (1H, m), 5.09-5.16 (2H, m), 7.27-7.40 (5H, m).

HPLC relative purity: 98.1% (RT: 5.22 min), column: Inertsil ODS-3, 4.6 mm×150 mm, pre-column: Inertsil ODS-3, 4.0 mm×10 mm, mobile phase: diluted phosphoric acid (1 in 1,000) (solution A), acetonitrile (solution B), 0 to 20 minutes; solution A:solution B=60:40 (isocratic), detection wavelength: 210 nm, column temperature: 30° C., flow rate: 1.0 mL/min

Reference Example 4

Benzyl (3R,4R)-3-((N-cyclopropyl-N-ethoxycarbonyl)aminomethyl)-4-hydroxypyrrolidine-1-carboxylate 10.0 mL of tetrahydrofuran was added to 1.00 g (3.06 mmol) of benzyl (3S,4R)-3-(cyclopropylaminomethyl)-4-hydroxypyrrolidine-1-carboxylate hydrochloride to suspend the same, and a sodium hydrogen carbonate solution (a solution in which 0.643 g of sodium hydrogen carbonate was dissolved in 10.0 mL of water) was added under stirring.

0.366 mL of ethyl chloroformate was added dropwise to the reaction mixture, followed by stirring for 2 hours at 40 to 43° C. The reaction mixture was extracted with 10.0 mL of ethyl acetate, the organic layer was separated, and anhydrous magnesium sulfate was added thereto. The anhydrous magnesium sulfate was separated by filtration and washed with 5.0 mL of ethyl acetate.

The filtrate and the washing were combined and concentrated under reduced pressure to obtain 1.06 g of benzyl (3R,4R)-3-((N-cyclopropyl-N-ethoxycarbonyl)aminomethyl)-4-hydroxypyrrolidine-1-carboxylate as a colorless oil.

$^1$H-NMR (CDCl$_3$, 400 MHz) δ: 0.59-0.69 (2H, m), 0.75-0.82 (2H, m), 1.22-1.32 (3H, m), 2.27-2.43 (1H, m), 2.54-2.61 (1H, m), 3.15-3.46 (4H, m), 3.65-3.79 (2H, m), 4.09-4.18 (3H, m), 5.10-5.17 (2H, m), 7.26-7.40 (5H, m).

HPLC relative purity: 98.6% (RT: 3.43 min), column: Inertsil ODS-3, 4.6 mm×150 mm, pre-column: Inertsil ODS-3, 4.0 mm×10 mm, mobile phase: diluted phosphoric acid (1 in 1,000) (solution A), acetonitrile (solution B), 0 to 20 minutes; solution A:solution B=60:40 (isocratic), detection wavelength: 210 nm, column temperature: 30° C., flow rate: 1.0 mL/min

Example 1

Benzyl (3R,4R)-3-(N-cyclopropyl-N-(2-nitrobenzenesulfonyl)aminomethyl)-4-hydroxypyrrolidine-1-carboxylate was dissolved in a solvent (toluene, 10-fold amount), a base (DBU, 1.5 equivalents) and a fluorinating agent (nonafluorobutane-1-sulfonyl fluoride, 1.5 equivalents) were sequentially added thereto, followed by stirring for 2 hours at 25° C. HPLC measurement of this reaction mixture was performed. The results are shown in Table 1.

Example 2

The reaction was carried out in the same manner as that of Example 1, using benzyl (3R,4R)-3-(N-cyclopropyl-N-(4-nitrobenzenesulfonyl)aminomethyl)-4-hydroxypyrrolidine-1-carboxylate as the substrate, and HPLC measurement of this reaction mixture was performed. The results are shown in Table 1.

Comparative Example 1

The reaction was carried out in the same manner as that of Example 1, using benzyl (3S,4R)-3-((N-benzyl-N-cyclopropypaminomethyl)-4-hydroxypyrrolidine-1-carboxylate as the substrate, and HPLC measurement of this reaction mixture was performed. The results are shown in Table 1.

Comparative Example 2

The reaction was carried out in the same manner as that of Example 1, using benzyl (3R,4R)-3-(N-cyclopropyl-N-(tert-butoxycarbonyl)aminomethyl)-4-hydroxypyrrolidine-1-carboxylate as the substrate, and HPLC measurement of this reaction mixture was performed. The results are shown in Table 1.

Comparative Example 3

The reaction was carried out in the same manner as that of Example 1, using benzyl (3R,4R)-3-((N-cyclopropyl-N-ethoxycarbonyl)aminomethyl)-4-hydroxypyrrolidine-1-carboxylate as the substrate, and HPLC measurement of this reaction mixture was performed. The results are shown in Table 1.

In Table 1, HPLC (%) is a value which is calculated such that the total area percentage (%) of the substrate, the target compound, the 3,4-elimination compound, and the 4,5-elimination compound to be 100%.

Area percentage of each component(%)=(area value of each component)/(total area value of each component)×100

For those in which an isolated yield of the target compound was obtained, the yields are listed in the remarks column. In addition, the measurement conditions of HPLC used are as follows.

HPLC measurement conditions of Example 1 and Example 2
Column: Inertsil ODS-3, 4.6 mm×150 mm, pre-column: Inertsil ODS-3, 4.0 mm×10 mm, mobile phase: diluted phosphoric acid (1 in 1,000) (solution A), acetonitrile (solution B), 0 to 20 minutes; solution A:solution B=60:40 (isocratic), detection wavelength: 220 nm, column temperature: 30° C., flow rate: 1.0 mL/min HPLC measurement conditions of Comparative Example 1
Column: Inertsil ODS-3, 4.6 mm×150 mm, pre-column: Inertsil ODS-3, 4.0 mm×10 mm, mobile phase: diluted phosphoric acid containing 5 mmol/L octanesulfonic acid (1 in 1,000) (solution A), acetonitrile (solution B), 0 to 40 minutes; solution A:solution B=65:35 (isocratic), detection wavelength: 210 nm, column temperature: 40° C., flow rate: 1.0 mL/min HPLC measurement conditions of Comparative Example 2 and Comparative Example 3
Column: Inertsil ODS-3, 4.6 mm×150 mm, pre-column: Inertsil ODS-3, 4.0 mm×10 mm, mobile phase: diluted phosphoric acid (1 in 1,000) (solution A), acetonitrile (solution B), 0 to 20 minutes; solution A:solution B=60:40 (isocratic), detection wavelength: 210 nm, column temperature: 30° C., flow rate: 1.0 mL/min

TABLE 1

| | HPLC (%) | | | | |
|---|---|---|---|---|---|
| | Substrate | Target Compound | 3,4-Elimination Compound | 4,5-Elimination Compound | Remarks |
| Example 1 | 0.2 | 94.1 | ND | 5.7 | 88% |
| Example 2 | ND | 95.6 | ND | 4.4 | 96% |
| Comparative Example 1 | 0.9 | 82.5 | 5.6 | 11.1 | — |
| Comparative Example 2 | 10.9 | 77.8 | ND | 11.2 | — |
| Comparative Example 3 | 9.6 | 78.3 | ND | 12.1 | — |

ND: not detected

As shown in Table 1, when a 2-nitrobenzenesulfonyl group (Example 1) and a 4-nitrobenzenesulfonyl group (Example 2) were used as the protecting group on the N-substituted-amino group [$PG^2$ in the general formula (1)], the reaction completed without the 3,4-elimination compound being observed at all, although the 4,5-elimination compound was formed in small amounts.

On the other hand, when a benzyl group (Comparative Example 1) was used, the amounts of the 3,4-elimination compound and the 4,5-elimination compound were increased, respectively. When a tert-butoxycarbonyl group (Comparative Example 2) and an ethoxycarbonyl group (Comparative Example 3) were used, the reaction was not complete and an increase of the amount of 4,5-elimination compound and other impurities was observed as well.

From these results, it was found that, when a nitrobenzenesulfonyl group was used as the protecting group on the N-substituted-amino group [$PG^2$ in the general formula (1)], the 3,4-elimination compound, which was formed when a benzyl group (Comparative Example 1) was used, was not formed, and the amount of 4,5-elimination compound formed was also small, in comparison with the cases of other protecting groups being used. That is, it was found that, a highly pure optically active syn-1-protected-3-(N-substituted-N-nitrobenzenesulfonylaminomethyl)-4-fluoropyrrolidine derivative may be obtained in high yield by fluorinating optically active anti-1-protected-3-(N-substituted-N-nitrobenzenesulfonylaminomethyl)-4-hydroxypyrrolidine using a fluorinating agent.

Hereinafter, in Table 2 to Table 4, the substrate refers to benzyl (3R,4R)-3-(N-cyclopropyl-N-(2-nitrobenzenesulfonyl)aminomethyl)-4-hydroxypyrrolidine-1-carboxylate, and the target compound refers to benzyl (3R,4S)-3-(N-cyclopropyl-N-(2-nitrobenzenesulfonyl)aminomethyl)-4-fluoropyrrolidine-1-carboxylate.

HPLC(%) is a value which is calculated such that the total area percentage(%) of the substrate, the target compound, and the 4,5-elimination compound to be 100%. Area percentage of each component(%)=(area value of each component)/(total area value of each component)×100

In addition, measurement conditions of HPLC and TLC used were as follows. HPLC conditions
Column: Inertsil ODS-3, 4.6 mm×150 mm, pre-column: Inertsil ODS-3, 4.0 mm×10 mm, mobile phase: diluted phosphoric acid (1 in 1,000) (solution A), acetonitrile (solution B), 0 to 20 minutes; solution A:solution B=60:40 (isocratic), detection wavelength: 220 nm, column temperature: 30° C., flow rate: 1.0 mL/min
TLC Conditions
Silica gel 60, ethyl acetate:n-hexane=2:1

Examples 3 to 7

Benzyl (3R,4R)-3-(N-cyclopropyl-N-(2-nitrobenzenesulfonyl)aminomethyl)-4-hydroxypyrrolidine-1-carboxylate was dissolved in the solvent listed in Table 2 (10-fold amount). The base listed in Table 2 (1.5 equivalents) and a fluorinating agent (nonafluorobutane-1-sulfonyl fluoride, 1.5 equivalents) were sequentially added thereto, followed by stirring for 2 hours at 25° C. HPLC measurement of this reaction mixture was performed. The results are shown in Table 2.

Comparative Examples 4 to 6

Benzyl (3R,4R)-3-(N-cyclopropyl-N-(2-nitrobenzene-sulfonyl)aminomethyl)-4-hydroxypyrrolidine-1-carboxylate was dissolved in the solvent listed in Table 2 (10-fold amount). The base listed in Table 2 (1.5 equivalents) and a fluorinating agent (nonafluorobutane-1-sulfonyl fluoride, 1.5 equivalents) were sequentially added thereto, followed by stirring for 2 hours at 25° C. HPLC measurement or a reaction monitoring by TLC of this reaction mixture was performed. The results are shown in Table 2.

TABLE 2

|  | Base | Solvent | HPLC (%) | | |
|---|---|---|---|---|---|
|  |  |  | Substrate | Target Compound | 4,5-Elimination Compound |
| Example 1 | DBU | toluene | 0.2 | 94.1 | 5.7 |
| Example 3 | DBN | toluene | ND | 84.0 | 16.0 |
| Example 4 | TMG | toluene | ND | 92.7 | 7.3 |
| Comparative Example 4 | $^i$Pr$_2$NEt | toluene |  | NT |  |
| Comparative Example 5 | 2,4,6-collidine | toluene |  | NT |  |
| Comparative Example 6 | DABCO | toluene | 28.0 | 44.2 | 27.9 |
| Example 5 | DBU | DME | ND | 92.6 | 7.4 |
| Example 6 | DBU | CH$_2$Cl$_2$ | ND | 89.7 | 10.2 |
| Example 7 | DBU | $^i$PrOAc | 3.3 | 92.6 | 5.1 |

ND: not detected
NT: It was confirmed by TLC that the reaction did not proceed, so HPLC measurement was not performed As shown in Table 2, the reaction also proceeded when 1,8-diazabicyclo[5.4.0]undec-7-ene (Example 1), 1,5-diazabicyclo[4.3.0]non-5-ene (Example 3) and 1,1,3,3-tetramethylguanidine (Example 4) were used as the base. On the other hand, when diisopropylethylamine (Comparative Example 4) and 2,4,6-collidine (Comparative Example 5) were used, the reaction did not proceed.

In addition, when 1,4-diazabicyclo[2.2.2]octane (Comparative Example 6) was used, the reaction was not complete, and the amount of 4,5-elimination compound was significantly increased, in comparison with the case in which 1,8-diazabicyclo[5.4.0]undec-7-ene (Example 1) was used.

From these results, it was found that by fluorinating the compound represented by the general formula (6) or it's enantiomer using the organic base having an amidine or guanidine structure as the base, the fluorination reaction can proceed and the fluorination reaction can be completed, therefore, by-production of the 4,5-elimination compound can be suppressed.

The reaction also proceeded when toluene (Example 1), 1,2-dimethoxyethane (Example 5), dichloromethane (Example 6), and isopropyl acetate (Example 7) were used as the solvent, however, the reaction was not complete when isopropyl acetate (Example 7) was used. In addition, it was found that, when toluene (Example 1) was used, the yield of the target compound was high, in comparison with those of Examples 5 to 7 and the amount of by-production of the 4,5-elimination compound was small.

From these results, it was found that toluene, 1,2-dimethoxyethane or dichloromethane is preferable as the solvent used in the fluorination reaction, and toluene is more preferable.

Examples 8 to 11

Benzyl (3R,4R)-3-(N-cyclopropyl-N-(2-nitrobenzene-sulfonyl)aminomethyl)-4-hydroxypyrrolidine-1-carboxylate was dissolved in toluene in the solvent amount listed in Table 3. A base (DBU, 1.5 equivalents) and a fluorinating agent (nonafluorobutane-1-sulfonyl fluoride, 1.5 equivalents) were sequentially added thereto, followed by stirring for 2 hours at the temperature listed in Table 3. HPLC measurement of this reaction mixture was performed. The results are shown in Table 3.

TABLE 3

|  | Solvent Amount (v/w) | Temperature (° C.) | HPLC (%) | | |
|---|---|---|---|---|---|
|  |  |  | Substrate | Target Compound | 4,5-Elimination Compound |
| Example 1 | 10 | 25 | 0.2 | 94.1 | 5.7 |
| Example 8 | 10 | 5 | ND | 95.7 | 4.3 |
| Example 9 | 5 | 5 | ND | 94.8 | 5.2 |
| Example 10 | 20 | 5 | ND | 98.2 | 1.8 |
| Example 11 | 40 | 5 | 31.9 | 67.0 | 1.1 |

ND: not detected

As shown in Table 3, as a result of the examination of reaction temperature, suppression of the formation of the 4,5-elimination compound was observed at 5° C. (Example 8), in comparison with the case of 25° C. (Example 1). From these results, it was found that by setting the reaction temperature of the fluorination reaction to be 10° C. or less, by-production of the 4,5-elimination compound may be effectively suppressed.

In addition, as a result of the examination of solvent amount, suppression of the formation of the 4,5-elimination compound was observed when the amount of the solvent was increased to 20-fold amount (Example 10) and 40-fold amount (Example 11), in comparison with the case of 10-fold amount (Example 8). On the other hand, if the amount of the solvent was decreased to 5-fold amount (Example 9), a slight increase of the formation of the elimination compound was observed. In addition, when the amount of the solvent was 40-fold amount (Example 11), the yield of the target compound was reduced, in comparison with the case of 20-fold amount (Example 10).

From these results, it was found that, in the fluorination reaction of the compound represented by the general formula (6) or it's enantiomer, the target compound can be obtained in high yield along with effectively suppressing the by-production of the 4,5-elimination compound by using 15- to 25-fold amount of the solvent with regard to the compound represented by the general formula (6) or it's enantiomer.

Example 12

Benzyl (3R,4R)-3-(N-cyclopropyl-N-(2-nitrobenzene-sulfonyl)aminomethyl)-4-hydroxypyrrolidine-1-carboxylate was dissolved in a solvent (toluene, 20-fold amount). A base (DBU, 1.5 equivalents) was added, after cooling to 5° C., a fluorinating agent (tridecafluorohexane-1-sulfonyl fluoride, 1.5 equivalents) was added, followed by stirring for 2 hours at the same temperature. HPLC measurement of this reaction mixture was performed. The results are shown in Table 4.

Example 13

Benzyl (3R,4R)-3-(N-cyclopropyl-N-(2-nitrobenzenesulfonyl)aminomethyl)-4-hydroxypyrrolidine-1-carboxylate was dissolved in a solvent (toluene, 20-fold amount). A base (DBU, 1.5 equivalents) was added, after cooling to 5° C., a fluorinating agent (heptadecafluorooctane-1-sulfonyl fluoride, 1.5 equivalents) was added, followed by stirring for 2 hours at the same temperature. HPLC measurement of this reaction mixture was performed. The results are shown in Table 4.

Comparative Example 7

Benzyl (3R,4R)-3-(N-cyclopropyl-N-(2-nitrobenzenesulfonyl)aminomethyl)-4-hydroxypynolidine-1-carboxylate was dissolved in a solvent (toluene, 20-fold amount). A base (DBU, 1.5 equivalents) was added, after cooling to 5° C., a fluorinating agent (p-toluenesulfonyl fluoride, 1.5 equivalents) was added, followed by stirring for 2 hours at the same temperature. The results are shown in Table 4.

TABLE 4

| | | HPLC (%) | |
|---|---|---|---|
| | Fluorinating Agent | Substrate | Target Compound | 4,5-Elimination Compound |
| Example 10 | $C_4F_9SO_2F$ | ND | 98.2 | 1.8 |
| Example 12 | $C_6F_{13}SO_2F$ | ND | 97.0 | 2.9 |
| Example 13 | $C_8F_{17}SO_2F$ | 0.3 | 94.7 | 5.0 |
| Comparative Example 7 | p-TolSO$_2$F | | NT | |

ND: not detected
NT: It was confirmed by TLC that the reaction did not proceed, so HPLC measurement was not performed When tridecafluorohexane-1-sulfonyl fluoride (Example 12) and heptadecafluorooctane-1-sulfonyl fluoride (Example 13) were used as the fluorinating agent, almost the same results were obtained, in comparison with a case of nonafluorobutane-1-sulfonyl fluoride (Example 10). On the other hand, when p-toluenesulfonyl fluoride (Comparative Example 7) which is not a nucleophilic fluorinating agent was used, the reaction did not proceed.

Hereinafter, in Table 5 to Table 8, HPLC (%) is an area percentage (%) of the target compound (benzyl (3S,4S)-3-(cyclopropylaminomethyl)-4-fluoropyrrolidine-1-carboxylate) at the end of the reaction (blank value derived from the solvent is corrected for). For those in which an isolated yield of the target compound was obtained, the yields are listed in the remarks column. In addition, the conditions of HPLC and TLC used were as follows.

HPLC Conditions
Column: Inertsil ODS-3, 4.6 mm×150 mm, pre-column: Inertsil ODS-3, 4.0 mm×10 mm, mobile phase: diluted phosphoric acid (1 in 1,000) (solution A), acetonitrile (solution B), 0 to 10 minutes; solution A:solution B=82:18 (isocratic), 10 to 30 minutes; solution A:solution B=82:18→20:80 (linear gradient), detection wavelength: 215 nm, column temperature: 30° C., flow rate: 1.0 mL/min
TLC Conditions
Silica gel 60, ethyl acetate:n-hexane:acetone=1:2:1

Example 14

Benzyl (3R,4S)-3-(N-cyclopropyl-N-(2-nitrobenzenesulfonyl)aminomethyl)-4-fluoropyrrolidine-1-carboxylate was dissolved in a solvent (N,N-dimethylformamide, 5-fold amount). A thiol (thioglycolic acid, 2 equivalents) and a base (lithium hydroxide monohydrate, 5 equivalents) were added thereto, followed by stirring for 2 hours at 25° C.

A sodium hydrogen carbonate solution was added to this reaction mixture, followed by extraction with ethyl acetate. Anhydrous sodium sulfate was added to the organic layer and it was allowed to stand at room temperature for several hours. After the anhydrous sodium sulfate was separated by filtration and washed with ethyl acetate, the filtrate and the washing were combined, and concentrated under reduced pressure, and HPLC measurement of the concentrated substance obtained was performed. The results are shown in Table 5.

Example 15

The reaction was carried out in the same manner as that of Example 14, using the solvent (5-fold amount) and the base (5 equivalents) listed in Table 5. The results are shown in Table 5.

Reference Examples 5 to 6

The reaction was carried out in the same manner as that of Example 14, using the solvent (5-fold amount) and the base (5 equivalents) listed in Table 5. The results are shown in Table 5.

TABLE 5

| | Thiol | Solvent | Base | HPLC (%) | Remarks |
|---|---|---|---|---|---|
| Example 14 | HSCH$_2$CO$_2$H | DMF | LiOH•H$_2$O | 88 | 72% |
| Example 15 | HSCH$_2$CO$_2$H | DMF | CsOH•H$_2$O | NT | Byproducts were formed, so HPLC measurement was not performed. |
| Reference Example 5 | HSCH$_2$CO$_2$H | acetone | LiOH•H$_2$O | NT | It was confirmed by TLC that the reaction did not proceed, so HPLC measurement was not performed. |
| Reference Example 6 | HSCH$_2$CO$_2$H | CH$_3$CN | LiOH•H$_2$O | NT | It was confirmed by TLC that the reaction did not proceed, so HPLC measurement was not performed. |

NT: not tested

In Table 5, the examination results for the cases in which thioglycolic acid was used as the thiol compound in the reaction of deprotecting the protecting group on the amino group of the compound represented by the general formula (7) or it's enantiomer using the thiol compound and the base are summarized.

As shown in Table 5, the target compound was able to be obtained by carrying out the reaction in DMF using lithium hydroxide monohydrate as the base (Example 14). On the other hand, when the reaction was carried out in DMF using cesium hydroxide monohydrate as the base, the reaction proceeded although a byproduct (a reduction compound of the nitro group) was formed (Example 15). In addition, when acetone (Reference Example 5) or acetonitrile (Reference Example 6) was used as the solvent, the reaction did not proceed.

From these results, in the deprotection reaction, it was found that, when thioglycolic acid was used as the thiol compound, using an alkali metal hydroxide as the base was preferable. In addition, it was found that, when the alkali metal hydroxide was used as the base, using an amide solvent as the solvent is preferable.

Example 16

Benzyl (3R,4S)-3-(N-cyclopropyl-N-(2-nitrobenzene-sulfonyl)aminomethyl)-4-fluoropyrrolidine-1-carboxylate was dissolved in a solvent (N,N-dimethylformamide, 5-fold amount). A thiol (1-dodecanethiol, 1.5 equivalents) and a base (lithium hydroxide monohydrate, 2 equivalents) were added thereto, and after stirring for 2 hours at 25° C., the temperature was raised, followed by stirring for 2 hours at 50° C.

Ethyl acetate was added to this reaction mixture and, followed by extraction with 3 mol/L hydrochloric acid. After the aqueous layer was made to be basic by adding sodium hydroxide solution, followed by extraction with ethyl acetate. Anhydrous sodium sulfate was added to the organic layer and it was allowed to stand at room temperature for several hours. After the anhydrous sodium sulfate was separated by filtration and washed with ethyl acetate, the filtrate and the washing were combined, and concentrated under reduced pressure, and HPLC measurement of the concentrated substance obtained was performed. The results are shown in Table 6.

Examples 17 to 18

Benzyl (3R,4S)-3-(N-cyclopropyl-N-(2-nitrobenzene-sulfonyl)aminomethyl)-4-fluoropyrrolidine-1-carboxylate was dissolved in a solvent (acetonitrile, 5-fold amount). The thiol (1.5 equivalents) and a base (cesium carbonate, 2.0 equivalents), listed in Table 6, were added thereto, followed by stirring for 2 hours at 25° C.

Ethyl acetate was added to this reaction mixture, followed by extraction with 3 mol/L hydrochloric acid. After the aqueous layer was made to be basic by adding sodium hydroxide solution, followed by extraction with ethyl acetate. Anhydrous sodium sulfate was added to the organic layer and it was allowed to stand at room temperature for several hours. After the anhydrous sodium sulfate was separated by filtration and washed with ethyl acetate, the filtrate and the washing were combined, and concentrated under reduced pressure, and HPLC measurement of the concentrated substance obtained was performed. The results are shown in Table 6.

Example 19

Benzyl (3R,4S)-3-(N-cyclopropyl-N-(2-nitrobenzene-sulfonyl)aminomethyl)-4-fluoropyrrolidine-1-carboxylate was dissolved in a solvent (acetonitrile, 5-fold amount). A thiol (2-carboxybenzenethiol, 2.0 equivalents) and a base (cesium carbonate, 5.0 equivalents) were added thereto, and after stirring for 2 hours at 25° C., the temperature was raised, followed by stirring for 2 hours at 50° C.

Water was added to this reaction mixture, followed by extraction with ethyl acetate. After the organic layer was washed with a sodium hydrogen carbonate solution, anhydrous sodium sulfate was added and it was allowed to stand at room temperature. After the anhydrous sodium sulfate was separated by filtration and washed with ethyl acetate, the filtrate and the washing were combined, and concentrated under reduced pressure, and HPLC measurement of the concentrated substance obtained was performed. The results are shown in Table 6.

Example 20

Benzyl (3R,4S)-3-(N-cyclopropyl-N-(2-nitrobenzene-sulfonyl)aminomethyl)-4-fluoropyrrolidine-1-carboxylate was dissolved in a solvent (acetonitrile, 5-fold amount). A thiol (4-carboxybenzenethiol, 2.0 equivalents) and a base (cesium carbonate, 5.0 equivalents) were added thereto, and after stirring for 2 hours at 25° C., the temperature was raised, followed by stirring for 2 hours at 50° C. The results are shown in Table 6.

TABLE 6

| | Thiol | Solvent | Base | HPLC (%) | Remarks |
| --- | --- | --- | --- | --- | --- |
| Example 14 | $HSCH_2CO_2H$ | DMF | $LiOH \cdot H_2O$ | 88 | 72% |
| Example 16 | $C_{12}H_{25}SH$ | DMF | $LiOH \cdot H_2O$ | 68 | — |
| Example 17 | $4\text{-}^tBu\text{—}C_6H_4SH$ | $CH_3CN$ | $Cs_2CO_3$ | 92 | 91% |
| Example 18 | $C_6H_5SH$ | $CH_3CN$ | $Cs_2CO_3$ | 97 | 75% |
| Example 19 | $2\text{-}(CO_2H)\text{—}C_6H_4SH$ | $CH_3CN$ | $Cs_2CO_3$ | 86 | 86% |
| Example 20 | $4\text{-}(CO_2H)\text{—}C_6H_4SH$ | $CH_3CN$ | $Cs_2CO_3$ | NT | It was confirmed by TLC that the reaction proceeded approximately 70%. |

NT: not tested

In Table 6, the examination results for the cases in which a variety of thiol compounds were used in the reaction of deprotecting the protecting group on the amino group of the compound represented by the general formula (7) or it's enantiomer using the thiol compound and the base are shown.

As shown in Table 6, when 1-dodecanethiol was used (Example 16) as the thiol compound in the deprotection reaction, the reaction proceeded although the yield of the target compound is decreased, in comparison with the case in which thioglycolic acid was used (Example 14). In addition, when 4-tert-butylbenzenethiol (Example 17) or benzenethiol (Example 18) was used, the reaction proceeded rapidly at 25° C. and yielded the highly pure target compound.

In addition, when 2-carboxy-benzenethiol (Example 19) or 4-carboxy-benzenethiol (Example 20) was used, the reaction also proceeded, however, when 4-carboxy-benzenethiol was used, the reaction was not complete.

From these results, in the deprotection reaction, it was found that the use of thioglycolic acid, a C1 to C24 alkylthiol or benzenethiol which may be substituted is preferable as the thiol compound.

Example 21

Benzyl (3R,4S)-3-(N-cyclopropyl-N-(2-nitrobenzenesulfonyl)aminomethyl)-4-fluoropyrrolidine-1-carboxylate was dissolved in a solvent (acetonitrile, 5-fold amount). A thiol (1-dodecanethiol, 1.5 equivalents) and a base (DBU, 2.0 equivalents) were added thereto, followed by stirring for 2 hours at 25° C.

Ethyl acetate was added to this reaction mixture, followed by extraction with 3 mol/L hydrochloric acid. After the aqueous layer was made to be basic by adding sodium hydroxide solution, followed by extraction with ethyl acetate. Anhydrous sodium sulfate was added to the organic layer and it was allowed to stand at room temperature for several hours. After the anhydrous sodium sulfate was separated by filtration and washed with ethyl acetate, the filtrate and the washing were combined, and concentrated under reduced pressure, and HPLC measurement of the concentrated substance obtained was performed. The results are shown in Table 7.

Example 22

Benzyl (3R,4S)-3-(N-cyclopropyl-N-(2-nitrobenzenesulfonyl)aminomethyl)-4-fluoropyrrolidine-1-carboxylate was dissolved in a solvent (acetonitrile, 5-fold amount). A thiol (1-dodecanethiol, 1.5 equivalents) and a base (TMG, 2.0 equivalents) were added thereto, and after stirring for 2 hours at 25° C., the temperature was raised, followed by stirring for 2 hours at 50° C.

Ethyl acetate was added to this reaction mixture, followed by extraction with 3 mol/L hydrochloric acid. After the aqueous layer was made to be basic by adding sodium hydroxide solution, followed by extraction with ethyl acetate. Anhydrous sodium sulfate was added to the organic layer and it was allowed to stand at room temperature for several hours. After the anhydrous sodium sulfate was separated by filtration and washed with ethyl acetate, the filtrate and the washing were combined, and concentrated under reduced pressure, and HPLC measurement of the concentrated substance obtained was performed. The results are shown in Table 7.

Example 23

Benzyl (3R,4S)-3-(N-cyclopropyl-N-(2-nitrobenzenesulfonyl)aminomethyl)-4-fluoropyrrolidine-1-carboxylate was dissolved in a solvent (acetonitrile, 5-fold amount). A thiol (1-dodecanethiol, 1.5 equivalents) and a base (cesium carbonate, 2.0 equivalents) were added thereto, and after stirring for 2 hours at 25° C., the temperature was raised, followed by stirring for 2 hours at 50° C. The results are shown in Table 7.

Comparative Example 8

Benzyl (3R,4S)-3-(N-cyclopropyl-N-(2-nitrobenzenesulfonyl)aminomethyl)-4-fluoropyrrolidine-1-carboxylate was dissolved in a solvent (tetrahydrofuran, 5-fold amount). A thiol (1-dodecanethiol, 1.5 equivalents) and a base (lithium tert-butoxide, 2.0 equivalents) were added thereto, followed by stirring for 2 hours at 25° C. The results are shown in Table 7.

TABLE 7

| | Thiol | Solvent | Base | HPLC (%) | Remarks |
|---|---|---|---|---|---|
| Example 16 | $C_{12}H_{25}SH$ | DMF | $LiOH \cdot H_2O$ | 68 | 81% |
| Example 21 | $C_{12}H_{25}SH$ | $CH_3CN$ | DBU | 80 | — |
| Example 22 | $C_{12}H_{25}SH$ | $CH_3CN$ | TMG | 88 | — |
| Example 23 | $C_{12}H_{25}SH$ | $CH_3CN$ | $Cs_2CO_3$ | NT | It was confirmed by TLC that the reaction was not complete. |
| Comparative Example 8 | $C_{12}H_{25}SH$ | THF | $LiO^tBu$ | NT | It was confirmed by TLC that the reaction did not proceed, so HPLC measurement was not performed. |

NT: not tested

In Table 7, the examination results for the case in which 1-dodecanethiol was used as the thiol compound in the reaction of deprotecting the protecting group on the amino group of the compound represented by the general formula (7) or it's enantiomer using the thiol compound and the base are summarized.

As shown in Table 7, when 1,8-diazabicyclo[5.4.0]undec-7-ene (Example 21), 1,1,3,3-tetramethylguanidine (Example 22), and cesium carbonate (Example 23) were used as the base, the reaction also proceeded. When cesium carbonate was used (Example 23), the reaction was not complete.

On the other hand, when lithium tert-butoxide (Comparative Example 8) was used, the reaction system became a complex reaction mixture. In addition, when lithium hydroxide monohydrate was used as the base (Example 16), separation between the base used and the product was easy, in comparison with the cases in which 1,8-diazabicyclo[5.4.0]undec-7-ene (Example 21) and 1,1,3,3-tetramethylguanidine (Example 22) were used.

From these results, in the deprotection reaction, it was found that using an alkali metal hydroxide as the base is preferable when a C1 to C24 alkylthiol is used as the thiol compound.

Example 24

Benzyl (3R,4S)-3-(N-cyclopropyl-N-(2-nitrobenzenesulfonyl)aminomethyl)-4-fluoropyrrolidine-1-carboxylate was dissolved in a solvent (acetonitrile:water=12:1, 5-fold amount). A thiol (4-tert-butylbenzenethiol, 1.5 equivalents) and a base (cesium carbonate, 2.0 equivalents) were added thereto, and after stirring for 2 hours at 25° C., the temperature was raised, followed by stirring for 2 hours at 50° C. The results are shown in Table 8.

Examples 25 to 26

Benzyl (3R,4S)-3-(N-cyclopropyl-N-(2-nitrobenzenesulfonyl)aminomethyl)-4-fluoropyrrolidine-1-carboxylate was dissolved in the solvent listed in Table 8 (5-fold amount). A thiol (4-tert-butylbenzenethiol, 1.5 equivalents) and a base (cesium carbonate, 2.0 equivalents) were added thereto, followed by stirring for 2 hours at 25° C.

Ethyl acetate was added to this reaction mixture, followed by extraction with 3 mol/L hydrochloric acid. After the aqueous layer was made to be basic by adding sodium hydroxide solution, followed by extraction with ethyl acetate. Anhydrous sodium sulfate was added to the organic layer and it was allowed to stand at room temperature for several hours. After the anhydrous sodium sulfate was separated by filtration and washed with ethyl acetate, the filtrate and the washing were combined, and concentrated under reduced pressure, and HPLC measurement of the concentrated substance obtained was performed. The results are shown in Table 8.

Examples 27 to 30

Benzyl (3R,4S)-3-(N-cyclopropyl-N-(2-nitrobenzenesulfonyl)aminomethyl)-4-fluoropyrrolidine-1-carboxylate was dissolved in the solvent listed in Table 8 (5-fold amount). A thiol (4-tert-butylbenzenethiol, 1.5 equivalents) and a base (potassium carbonate, 2.0 equivalents) were added thereto, and after stirring for 2 hours at 25° C., the temperature was raised, followed by stirring for 2 hours at 50° C.

Ethyl acetate was added to this reaction mixture, followed by extraction with 3 mol/L hydrochloric acid. After the aqueous layer was made to be basic by adding sodium hydroxide solution, followed by extraction with ethyl acetate. Anhydrous sodium sulfate was added to the organic layer and it was allowed to stand at room temperature for several hours. After the anhydrous sodium sulfate was separated by filtration and washed with ethyl acetate, the filtrate and the washing were combined, and concentrated under reduced pressure, and HPLC measurement of the concentrated substance obtained was performed. The results are shown in Table 8.

Example 32

Benzyl (3R,4S)-3-(N-cyclopropyl-N-(2-nitrobenzenesulfonyl)aminomethyl)-4-fluoropyrrolidine-1-carboxylate was dissolved in a solvent (tetrahydrofuran, 5-fold amount). A thiol (4-tert-butylbenzenethiol, 1.5 equivalents) and a base (potassium carbonate, 2.0 equivalents) were added thereto, followed by stirring for 2 hours at 25° C. The results are shown in Table 8.

Example 33

Benzyl (3R,4S)-3-(N-cyclopropyl-N-(2-nitrobenzenesulfonyl)aminomethyl)-4-fluoropyrrolidine-1-carboxylate was dissolved in a solvent (acetonitrile, 5-fold amount). A thiol (4-tert-butylbenzenethiol, 1.5 equivalents) and a base (potassium carbonate, 2.0 equivalents) were added thereto, and after stirring for 2 hours at 25° C., the temperature was raised, followed by stirring for 2 hours at 50° C. The results are shown in Table 8.

TABLE 8

|  | Thiol | Solvent | Base | HPLC (%) | Remarks |
| --- | --- | --- | --- | --- | --- |
| Example 17 | 4-$^t$Bu—$C_6H_4$SH | $CH_3CN$ | $Cs_2CO_3$ | 92 | 91% |
| Example 24 | 4-$^t$Bu—$C_6H_4$SH | $CH_3CN$—$H_2O$ (12:1) | $Cs_2CO_3$ | NT | It was confirmed by TLC that the reaction was not complete. |
| Example 25 | 4-$^t$Bu—$C_6H_4$SH | THF | $Cs_2CO_3$ | 95 | 81% |
| Example 26 | 4-$^t$Bu—$C_6H_4$SH | $^i$PrOH | $Cs_2CO_3$ | 94 | 94% |
| Example 27 | 4-$^t$Bu—$C_6H_4$SH | $^i$PrOH | $K_2CO_3$ | 94 | 79% |
| Example 28 | 4-$^t$Bu—$C_6H_4$SH | $^i$PrOH—THF (3:1) | $K_2CO_3$ | 94 | 76% |
| Example 29 | 4-$^t$Bu—$C_6H_4$SH | EtOH—THF (3:1) | $K_2CO_3$ | 93 | 68% |
| Example 30 | 4-$^t$Bu—$C_6H_4$SH | EtOH—THF (1:1) | $K_2CO_3$ | 94 | 72% |
| Example 31 | 4-$^t$Bu—$C_6H_4$SH | EtOH | $K_2CO_3$ | 95 | 74% |
| Example 32 | 4-$^t$Bu—$C_6H_4$SH | THF | $K_2CO_3$ | NT | It was confirmed by TLC that the reaction was not complete. |
| Example 33 | 4-$^t$Bu—$C_6H_4$SH | $CH_3CN$ | $K_2CO_3$ | NT | It was confirmed by TLC that the reaction was not complete. |

NT: not tested

Example 31

Benzyl (3R,4S)-3-(N-cyclopropyl-N-(2-nitrobenzenesulfonyl)aminomethyl)-4-fluoropyrrolidine-1-carboxylate was dissolved in a solvent (ethanol, 5-fold amount). A thiol (4-tert-butylbenzenethiol, 1.5 equivalents) and a base (potassium carbonate, 2.0 equivalents) were added thereto, followed by stirring for 2 hours at 25° C.

Ethyl acetate was added to this reaction mixture, followed by extraction with 3 mol/L hydrochloric acid. After the aqueous layer was made to be basic by adding sodium hydroxide solution, followed by extraction with ethyl acetate. Anhydrous sodium sulfate was added to the organic layer and it was allowed to stand at room temperature for several hours. After the anhydrous sodium sulfate was separated by filtration and washed with ethyl acetate, the filtrate and the washing were combined, and concentrated under reduced pressure, and In Table 8, the examination results for the case in which 4-tert-butylbenzenethiol was used as the thiol compound in the reaction of deprotecting the protecting group on the amino group of the compound represented by the general formula (7) or it's enantiomer using the thiol compound and the base are summarized.

As shown in Table 8, when cesium carbonate was used as the base, the reaction completed even in tetrahydrofuran (Example 25) or 2-propanol (Example 26). The reaction was not complete in aqueous acetonitrile (Example 24).

When potassium carbonate was used as the base, the reaction completed when a lower alcohol (Examples 27 and 31) or a mixed solvent of a lower alcohol and tetrahydrofuran (Examples 28 to 30). On the other hand, the reaction was not complete in tetrahydrofuran (Example 32) and acetonitrile (Example 33).

From these results, it was found that, in the deprotection reaction, using an alkali metal carbonate as the base was preferable when benzenethiol which may be substituted was used as the thiol compound. In addition, it was found that using a lower alcohol, tetrahydrofuran, or a mixed solvent of these as the solvent is preferable when an alkali metal carbonate was used as the base.

Example 34

Benzyl (3R,4S)-3-(N-cyclopropyl-N-(2-nitrobenzenesulfonyl)aminomethyl)-4-fluoropyrrolidine-1-carboxylate 300 mL of toluene was added to 15.1 g (corresponding to 30.6 mmol) of crude benzyl (3R,4R)-3-(N-cyclopropyl-N-(2-nitrobenzenesulfonyl)aminomethyl)-4-hydroxypyrmlidine-1-carboxylate synthesized using the method of Reference Example 1, followed by heating to an inner temperature of 45 to 50° C. and dissolved, and 6.85 mL (45.9 mmol) of 1,8-diazabicyclo[5.4.0]undec-7-ene was added thereto at an inner temperature of 20 to 25° C., followed by cooling to an inner temperature of −20 to 0° C. 8.24 mL (45.9 mmol) of nonafluorobutane-1-sulfonyl fluoride was added thereto at an inner temperature of −20 to 0° C., followed by stirring for 2 hours at an inner temperature of −20 to 0° C.

200 mL of 1 mol/L hydrochloric acid and 100 mL of toluene were added to the reaction mixture, and the organic layer was separated. The organic layer was washed with 100 mL of 1 mol/L hydrochloric acid and with 200 mL of 6% sodium hydrogen carbonate solution sequentially. Anhydrous magnesium sulfate was added to the organic layer and it was allowed to stand for several hours. The anhydrous magnesium sulfate was filtered and washed with 50.0 mL of toluene.

After the filtrate and the washing were combined and concentrated under reduced pressure, it was concentrated again under reduced pressure with adding 40.0 mL of tetrahydrofuran to obtain 14.7 g of benzyl (3R,4S)-3-(N-cyclopropyl-N-(2-nitrobenzenesulfonyl)aminomethyl)-4-fluoropyrrolidine-1-carboxylate as a yellow oil.

$^1$H-NMR (CDCl$_3$, 400 MHz) δ: 0.62-0.77 (4H, m), 2.49-2.54 (2H, m), 2.68-2.83 (1H, m), 3.25 (1H, ddd, J=6.3, 11.0, 28.3 Hz), 3.44-3.59 (2H, m), 3.62-3.93 (4H, m), 5.11-5.25 (3H, m), 7.30-7.40 (5H, m), 7.61-7.65 (1H, m), 7.69-7.77 (2H, m), 8.11-8.14 (1H, m).

HPLC relative purity: 88.4% (retention time: 8.69 minutes), column: Inertsil ODS-3, 4.6 mm×150 mm, pre-column: Inertsil ODS-3, 4.0 mm×10 mm, mobile phase: diluted phosphoric acid (1 in 1,000) (solution A), acetonitrile (solution B), 0 to 20 minutes; solution A:solution B=60:40 (isocratic), detection wavelength: 220 nm, column temperature: 30° C., flow rate: 1.0 mL/min Example 35

Benzyl (3S,4S)-3-(cyclopropylaminomethyl)-4-fluoropyrrolidine-1-carboxylate hydrochloride 14.7 g (corresponding to 30.6 mmol) of benzyl (3R,4S)-3-(N-cyclopropyl-N-(2-nitrobenzenesulfonyl)aminomethyl)-4-fluoropyrrolidine-1-carboxylate synthesized using the method of Example 34 was dissolved in 40.0 mL of tetrahydrofuran, and 40.0 mL of ethanol, 8.46 g (61.2 mmol) of potassium carbonate and 7.92 mL (45.9 mmol) of 4-tert-butylbenzenethiol were sequentially added thereto, followed by stirring for 2 hours at an inner temperature of 45 to 55° C.

100 mL of 3 mol/L hydrochloric acid and 20.0 mL of n-haxane were added to the reaction mixture, and the aqueous layer was separated. The organic layer was extracted with 50.0 mL of 1 mol/L hydrochloric acid, combined with the aqueous layer, and washed with 50.0 mL of n-hexane. 100 mL of 5 mol/L sodium hydroxide solution was added to the aqueous layer making it basic, followed by extraction with 300 mL of tert-butyl methyl ether.

Anhydrous magnesium sulfate was added to the organic layer and it was allowed to stand for several hours. The anhydrous magnesium sulfate was filtered and washed with 50.0 mL of tert-butyl methyl ether. The filtrate and the washing were combined and concentrated under reduced pressure. 8.09 g of the residue (total amount) was dissolved in 40.5 mL of tert-butyl methyl ether and 20.2 mL of 5% hydrogen chloride/methanol was added at room temperature, followed by heating, and 40.5 mL of diisopropyl ether was added thereto at an inner temperature of 35 to 45° C.

After the crystallization, stirring was carried out for 30 minutes at almost the temperature at which the crystallization occurs. 40.5 mL of diisopropyl ether was added, and after stirring for 1 hour and cooled, followed by stirring for 0.5 hours at an inner temperature of 1 to 10° C. The precipitated solid was separated by filtration and was washed with 40.5 mL of diisopropyl ether. The solid was dried under reduced pressure at 40° C. to obtain 6.58 g (3 steps yield 65%) of benzyl (3S,4S)-3-(cyclopropylaminomethyl)-4-fluoropyrrolidine-1-carboxylate hydrochloride as a white powder.

Melting point (hot plate method): 161.7 to 162.9° C. (decomposition).

$[α]_D^{26}$ 5.4° (c1.01, methanol).

$^1$H-NMR (DMSO-d$_6$, 400 MHz) δ: 0.69-0.75 (2H, m), 0.79-0.97 (2H, m), 2.67-2.87 (2H, m), 3.08-3.20 (2H, m), 3.25-3.31 (1H, m), 3.57-3.82 (3H, m), 5.06-5.12 (2H, m), 5.35 (1H, dd, J=2.4, 53.0 Hz), 7.30-7.42 (5H, m), 9.34 (2H, brs).

HPLC relative purity: 93.8% (retention time: 10.78 minutes), column: Inertsil ODS-3, 4.6 mm×150 mm, pre-column: Inertsil ODS-3, 4.0 mm×10 mm, mobile phase: diluted phosphoric acid (1 in 1,000) (solution A), acetonitrile (solution B), 0 to 10 minutes; solution A:solution B=82:18 (isocratic), 10 to 30 minutes; solution A:solution B=82:18→20:80 (linear gradient), detection wavelength: 210 nm, column temperature: 30° C., flow rate: 1.0 mL/min Reference Example 8

Benzyl (3S,4S)-3-(N-cyclopropyl-N-(2-nitrobenzenesulfonyl)aminomethyl)-4-hydroxypyrrolidine-1-carboxylate 4.00 g (12.2 mmol) of benzyl (3R,4S)-3-(cyclopropylaminomethyl)-4-hydroxypyrrolidine-1-carboxylate hydrochloride was dissolved in 32 mL of 1,2-dimethoxyethane, then, a sodium hydrogen carbonate solution (a solution in which 2.57 g (30.6 mmol) of sodium hydrogen carbonate was dissolved in 40 mL of water) was added, and followed by stirring for 0.5 hours at room temperature.

A solution of 3.39 g (15.3 mmol) of 2-nitrobenzenesulfonyl chloride in 8 mL of 1,2-dimethoxyethane was added dropwise to the mixture, followed by stirring for 2 hours at 35° C. 40 mL of tert-butyl methyl ether was added to the reaction mixture under stirring, and after it was allowed to stand, the organic layer was separated.

Anhydrous magnesium sulfate was added to the organic layer. The anhydrous magnesium sulfate was filtered and washed with 20 mL of tert-butyl methyl ether. The filtrate and the washing were combined, and concentrated under reduced pressure to obtain 6.25 g (quantitative) of benzyl (3S,4S)-3-

(N-cyclopropyl-N-(2-nitrobenzenesulfonyl)aminomethyl)-4-hydroxypyrrolidine-1-carboxylate as a yellow oil.

$[\alpha]_D^{25}$ −53.6° (c1.11, CHCl$_3$)

$^1$H-NMR (CDCl$_3$, 400 MHz) δ: 0.52-0.78 (4H, m), 2.48-2.71 (2H, m), 3.17-3.28 (2H, m), 3.31-3.39 (1H, m), 3.41-3.60 (2H, m), 3.68-3.86 (2H, m), 4.25-4.42 (1H, m), 5.14 (2H, s), 7.28-7.40 (5H, m), 7.61-7.76 (3H, m), 8.12-8.15 (1H, m).

HPLC relative purity: 94.0% (RT: 11.5 min), column: CERI L-column2 ODS2, 4.6 mm×250 mm (3 μm), pre-column: CERI L-column2 ODS, 4.0 mm×10 mm (3 μm), mobile phase: acetonitrile (solution C), phosphate buffer solution of pH 6.9 (solution D), 0 to 40 minutes; solution C:solution D=50:50-40:20 (linear gradient), detection wavelength: 210 nm, column temperature: 40° C., flow rate: 0.75 mL/min.

Example 36

Benzyl (3S,4R)-3-(N-cyclopropyl-N-(2-nitrobenzenesulfonyl)aminomethyl)-4-fluoropyrrolidine-1-carboxylate 120 mL of toluene was added to 6.25 g (corresponding to 12.2 mmol) of crude benzyl (3S,4S)-3-(N-cyclopropyl-N-(2-nitrobenzenesulfonyl)aminomethyl)-4-hydroxypyrrolidine-1-carboxylate synthesized using the method of Reference Example 8, and it was heated to an inner temperature of 50° C. and dissolved, followed by cooling to an inner temperature of 20 to 25° C. 2.75 mL (18.4 mmol) of 1,8-diazabicyclo[5.4.0]undec-7-ene was added to the mixture, followed by cooling to an inner temperature of −16° C. 3.23 mL (18.4 mmol) of nonafluorobutane-1-sulfonyl fluoride was added dropwise at an inner temperature of −16 to −10° C., followed by stirring for 2 hours at an inner temperature of −10 to 4° C.

80 mL of 1 mol/L hydrochloric acid and 40 mL of toluene were added to the reaction mixture, and the organic layer was separated. The organic layer was washed with 40 mL of 1 mol/L hydrochloric acid and with 80 mL of 6% sodium hydrogen carbonate solution sequentially, and then it was dried over anhydrous magnesium sulfate. The anhydrous magnesium sulfate was filtered and the residue was washed with 20 mL of toluene.

The filtrate and the washing were combined, and concentrated under reduced pressure to obtain 6.05 g (quantitative) of benzyl (3S,4R)-3-(N-cyclopropyl-N-(2-nitrobenzenesulfonyl)aminomethyl)-4-fluoropyrrolidine-1-carboxylate as a yellow oil.

$[\alpha]_D^{27}$ 11.0° (c1.13, CHCl$_3$).

$^1$H-NMR (CDCl$_3$, 400 MHz) δ: 0.59-0.80 (4H, m), 2.49-2.54 (1H, m), 2.63-2.86 (1H, m), 3.25 (1H, dt, J=8.5, 20.0 Hz), 3.43-3.60 (2H, m), 3.62-3.73 (1H, m), 3.77-3.93 (2H, m), 5.14 (2H, s), 5.18 (2H, d, J=52.9 Hz), 7.30-7.40 (5H, m), 7.63 (1H, td, J=1.8, 7.1 Hz), 7.67-7.77 (2H, m), 8.12 (1H, dd, J=1.8, 7.5 Hz).

HPLC relative purity: 88.4% (RT: 17.9 min), column: CERI L-column2 ODS2, 4.6 mm×250 mm (3 μm), pre-column: CERI L-column2 ODS, 4.0 mm×10 mm (3 μm), mobile phase: acetonitrile (solution C), phosphate buffer solution of pH 6.9 (solution D), 0 to 40 minutes; solution C:solution D=50:50-+80:20 (linear gradient), detection wavelength: 210 nm, column temperature: 40° C., flow rate: 0.75 mL/min.

Example 37

Benzyl (3R,4R)-3-(cyclopropylaminomethyl)-4-fluoropyrrolidine-1-carboxylate hydrochloride 6.05 g (corresponding to 12.2 mmol) of crude benzyl (3S,4R)-3-(N-cyclopropyl-N-(2-nitrobenzenesulfonyl)aminomethyl)-4-fluoropyrrolidine-1-carboxylate synthesized using the method of Example 36 was dissolved in 16 mL of tetrahydrofuran, and 16 mL of ethanol and 3.38 g (24.2 mmol) of potassium carbonate were added.

3.17 mL (18.4 mmol) of 4-tert-butylbenzenethiol was added dropwise to the mixture at an inner temperature of around 30° C., followed by stirring for 2 hours at an inner temperature of 50° C. The reaction mixture was cooled to a room temperature, and after 40 mL of 3 mol/L hydrochloric acid and 8 mL of n-hexane were added, the aqueous layer was separated.

The organic layer was extracted with 20 mL of 1 mol/L hydrochloric acid and after being combined with the aqueous layer, it was washed with 20 mL of n-hexane. The aqueous layer was made to be basic by adding 40 mL of 5 mol/L sodium hydroxide solution, followed by extraction with 120 mL of tert-butyl methyl ether. Anhydrous magnesium sulfate was added to the organic layer and was dried. The anhydrous magnesium sulfate was filtered and the residue was washed with 2 mL of tert-butyl methyl ether.

The filtrate and the washing were combined and concentrated under reduced pressure. The residue (3.58 g) was dissolved in 20 mL of tert-butyl methyl ether and 11.2 mL of 5% hydrogen chloride/methanol was added at an inner temperature of 24 to 28° C., followed by heating to an inner temperature of 40° C. 20 mL of diisopropyl ether was added to the mixture at an inner temperature of around 40° C. and after the crystallization, stirring was carried out for 30 minutes at the same temperature.

20 mL of diisopropyl ether was added to the mixture, followed by stirring for 1 hour at around 40° C., and then it was gradually cooled to an inner temperature of 10° C. The precipitated solid was separated by filtration and was washed with 20 mL of diisopropyl ether. The solid was dried under reduced pressure at 40° C. to obtain 3.23 g (3 steps yield 80%, calculated from benzyl (3R,4S)-3-(cyclopropylaminomethyl)-4-hydroxypyrrolidine-1-carboxylate hydrochloride) of benzyl (3R,4R)-3-(cyclopropylaminomethyl)-4-fluoropyrrolidine-1-carboxylate hydrochloride as a white powder.

Melting point (hot plate method): 160.8 to 162.4° C. (decomposition)

$[\alpha]_D^{26}$ −5.3° (c1.01, methanol).

$^1$H-NMR (DMSO-d$_6$, 400 MHz) δ: 0.68-0.80 (2H, m), 0.86-1.00 (2H, m), 2.65-2.90 (2H, m), 3.03-3.37 (3H, m), 3.52-3.72 (2H, m), 3.73-3.84 (1H, m), 5.09 (2H, s), 5.36 (1H, d, J=52.6 Hz), 7.28-7.42 (5H, m), 9.37 (2H, brs).

HPLC relative purity: 94.7% (RT: 9.7 min), column: CERI L-column2 ODS2, 4.6 mm×250 mm (3 μm), pre-column: CERI L-column2 ODS, 4.0 mm×10 mm (3 μm), mobile phase: acetonitrile (solution A), phosphate buffer solution of pH 6.9 (solution B), 0 to 40 minutes; solution A:solution B=50:50→80:20 (linear gradient), detection wavelength: 210 nm, column temperature: 40° C., flow rate: 0.75 mL/min.

The present invention has been described in detail using specific embodiments, however, it is apparent to those skilled in the prior art that a variety of changes and modifications are possible without departing from the scope and intent of the present invention. Incidentally, it should be noted that the present application is based on Japanese Patent Application filed May 31, 2010 (Japanese Patent Application No. 2010-123889) and the entire content of which is incorporated herein by reference.

INDUSTRIAL APPLICABILITY

The present invention is an industrially advantageous method for producing optically active syn-3-(N-substitutedaminomethyl)-4-fluoropyrrolidine or their salts which may be used as intermediates in the production of pharmaceuticals at low cost. The present invention is useful in terms that a 7-(3-(cyclopropylaminomethyl-4-fluoropyrrolidinyl) quinolone carboxylic acid derivative which is safe, shows potent antibacterial activity, and is effective to resistant bacteria on which conventional antibacterial agents hardly show their effects may be advantageously produced industrially.

The invention claimed is:

1. A method for producing a compound represented by the general formula (7) or it's enantiomer, or their salts, comprising step 1:

(Step 1) a process of fluorinating a compound represented by the general formula (6) or it's enantiomer using a nucleophilic fluorinating agent and an organic base having an amidine or guanidine structure,

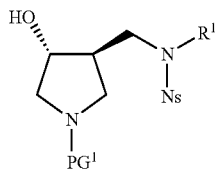

(6)

[wherein, in the general formula (6), $PG^1$ represents a protecting group for an amino group, $R^1$ represents a C1 to C6 alkyl group which may be substituted or a C3 to C8 cycloalkyl group which may be substituted, and Ns represents a 2-nitrobenzenesulfonyl group or a 4-nitrobenzenesulfonyl group],

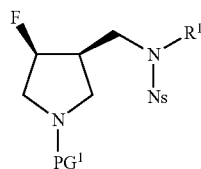

(7)

[wherein, in the general formula (7), $PG^1$ represents a protecting group for an amino group, $R^1$ represents a C1 to C6 alkyl group which may be substituted or a C3 to C8 cycloalkyl group which may be substituted, and Ns represents a 2-nitrobenzenesulfonyl group or a 4-nitrobenzenesulfonyl group].

2. A method for producing a compound represented by the general formula (8) or it's enantiomer, or their salts, comprising step 1 and step 2:

(Step 1) a process of fluorinating a compound represented by the general formula (6) or it's enantiomer using a nucleophilic fluorinating agent and an organic base having an amidine or guanidine structure; and (Step 2) a process of deprotecting a protecting group on the amino group of the compound represented by the general formula (7) or it's enantiomer, or their salts obtained in step 1 using a thiol compound and a base,

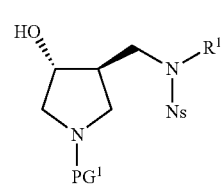

(6)

[wherein, in the general formula (6), $PG^1$ represents a protecting group for an amino group, $R^1$ represents a C1 to C6 alkyl group which may be substituted or a C3 to C8 cycloalkyl group which may be substituted, and Ns represents a 2-nitrobenzenesulfonyl group or a 4-nitrobenzenesulfonyl group],

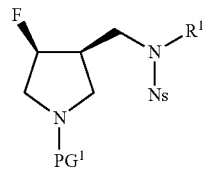

(7)

[wherein, in the general formula (7), $PG^1$ represents a protecting group for an amino group, $R^1$ represents a C1 to C6 alkyl group which may be substituted or a C3 to C8 cycloalkyl group which may be substituted, and Ns represents a 2-nitrobenzenesulfonyl group or a 4-nitrobenzenesulfonyl group],

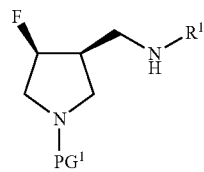

(8)

[wherein in the general formula (8), $PG^1$ represents a protecting group for an amino group, $R^1$ represents a C1 to C6 alkyl group which may be substituted or a C3 to C8 cycloalkyl group which may be substituted].

3. The production method according to claim 1 or 2, wherein, in step 1, a perfluoroalkanesulfonyl fluoride is used as the nucleophilic fluorinating agent.

4. The production method according to claim 3, wherein the perfluoroalkanesulfonyl fluoride is nonafluorobutane-1-sulfonyl fluoride.

5. The production method according to claim 1 or 2, wherein, in step 1, a reaction temperature is 10° C. or less.

6. The production method according to claim 1 or 2, wherein, in step 1, a solvent is used 15- to 25-fold amount of the compound represented by the general formula (6) or it's enantiomer.

7. The production method according to claim 1 or 2, wherein, in step 1, tetramethylguanidine, 1,8-diazabicyclo[5.4.0]undec-7-ene, or 1,5-diazabicyclo[4.3.0]non-5-ene is used as the organic base.

8. The production method according to claim 2, wherein, in step 2, the thiol compound is thioglycolic acid, a C1 to C24 alkylthiol or benzenethiol which may be substituted.

9. The production method according to claim 2, wherein, in step 2, the base is an alkali metal hydroxide, an alkali metal carbonate, or an organic base having an amidine or guanidine structure.

10. The production method according to claim 2, 8 or 9, wherein, in step 2, the thiol compound is thioglycolic acid or C1 to C24 alkylthiol, and the base is alkali metal hydroxide.

11. The production method according to claim 10, wherein the C1 to C24 alkylthiol is 1-dodecanethiol, and the alkali metal hydroxide is lithium hydroxide.

12. The production method according to claim 10, wherein, in step 2, N,N-dimethylformamide, N-methylpyrrolidone or N,N-dimethylacetamide is used as a reaction solvent.

13. The production method according to claim 12, wherein, in step 2, the N,N-dimethylformamide is used as the reaction solvent.

14. The production method according to claim 2, 8 or 9, wherein, in step 2, the thiol compound is benzenethiol which may be substituted, and the base is alkali metal carbonate.

15. The production method according to claim 14, wherein the benzenethiol which may be substituted is 4-tert-butylbenzenethiol, and the alkali metal carbonate is potassium carbonate or cesium carbonate.

16. The production method according to claim 14, wherein, in step 2, a lower alcohol, an ether solvent, a nitrile solvent, or a mixed solvent of these is used as a reaction solvent.

17. The production method according to claim 16, wherein a mixed solvent of the lower alcohol and the ether solvent is used as the reaction solvent.

18. The production method according to claim 16, wherein the lower alcohol is ethanol or 2-propanol, and the ether solvent is tetrahydrofuran.

19. The production method according to claim 17, wherein the lower alcohol is ethanol or 2-propanol, and the ether solvent is tetrahydrofuran.

* * * * *